(12) United States Patent
Levitzki et al.

(10) Patent No.: US 6,673,798 B2
(45) Date of Patent: *Jan. 6, 2004

(54) PDGF RECEPTOR KINASE INHIBITORY COMPOUNDS, THEIR PREPARATION, PURIFICATION AND PHARMACEUTICAL COMPOSITIONS INCLUDING SAME

(75) Inventors: Alexander Levitzki, Jerusalem (IL); Aviv Gazit, Jerusalem (IL); Shmuel Banai, Jerusalem (IL); David S. Gertz, Jerusalem (IL); Gershon Golomb, Efrat (IL); Frank D. Boehmer, Dorndorf (DE); Johannes Waltenberger, Ulm (DE)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 28 days.

This patent is subject to a terminal disclaimer.

(21) Appl. No.: 09/828,602

(22) Filed: Apr. 9, 2001

(65) Prior Publication Data

US 2002/0028817 A1 Mar. 7, 2002

Related U.S. Application Data

(63) Continuation of application No. 09/436,651, filed on Nov. 9, 1999, now Pat. No. 6,358,954.

(51) Int. Cl.$^7$ .................. A61K 31/519; A61K 31/4985; C07D 471/12
(52) U.S. Cl. .................. 514/250; 514/267; 544/247; 544/250; 544/251; 544/343; 544/345
(58) Field of Search ................ 514/250, 267; 544/247, 251, 343, 345, 250

(56) References Cited

U.S. PATENT DOCUMENTS 4,304,846 A * 12/1981 Marthaler et al. .......... 430/392
6,358,954 B1 * 3/2002 Levitzki et al. ............. 514/250

* cited by examiner

Primary Examiner—Mukund J. Shah
Assistant Examiner—Tamthom N. Truong
(74) Attorney, Agent, or Firm—G. E. Ehrlich (1995) Ltd.

(57) ABSTRACT

A purified tyrphostin of a general formula:

(Compound I)

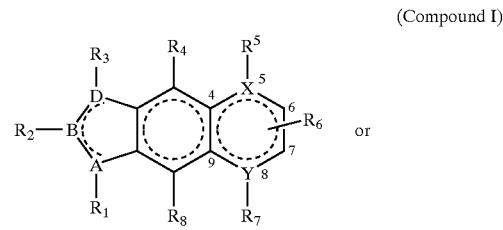

or (Compound II)

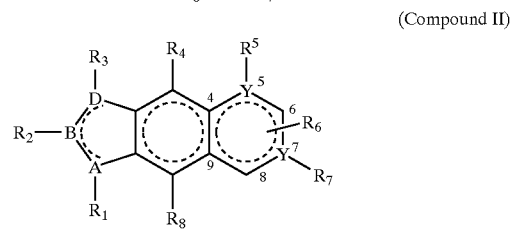

wherein, for Compound I, $R_6$ is either at position 6 or at position 7, or, for Compound II, $R_6$ is either at position 6 or at position 8.

31 Claims, 12 Drawing Sheets

US 6,673,798 B2

PDGF RECEPTOR KINASE INHIBITORY COMPOUNDS, THEIR PREPARATION, PURIFICATION AND PHARMACEUTICAL COMPOSITIONS INCLUDING SAME

This is a continuation of U.S. patent application Ser. No. 09/436,651, filed Nov. 9, 1999 now U.S. Pat. No. 6,358,954 B1.

FIELD AND BACKGROUND OF THE INVENTION

The present invention relates to PDGF receptor kinase inhibitory compounds and pharmaceutical compositions such as, but not limited to, slow release compositions. More particularly, the present invention relates to enriched or purified geometrical isomers of compounds of the quinoxaline family known to be PDGF receptor kinase inhibitors, compositions including same, methods of their synthesis, purification and formulation and their use for treatment of proliferative malignant and non-malignant diseases or disorders, such as, but not limited to, psoriasis, hepatic cirrhosis, diabetes, atherosclerosis, restenosis, vascular graft restenosis, in-stent stenosis, angiogenesis, ocular diseases, pulmonary fibrosis, obliterative bronchiolitis, glomerular nephritis, rheumatoid arthritis and PDGF receptor associated malignancies, such as, but not limited to, leukemias and lymphomas.

Platelet-derived growth factor (PDGF) is a potent mitogen for mesenchymal, glial, and capillary endothelial cells (for reviews, see, [1] and [2]). The three isoforms of PDGF, PDGF-AA, PDGF-AB, and PDGF-BB, interact differentially with structurally related receptors designated PDGF α- and β-receptors. Each of these receptors has an extracellular part featuring five immunoglobulin-like domains, a lipophilic transmembrane domain and an intracellular part with a tyrosine kinase domain containing a characteristic insert amino acid sequence [3–5]. The tyrosine kinase activity of these receptors is essential for transmission of the mitogenic signal into the cell [6].

PDGF and its receptors participate in various physiological processes such as embryonal development and wound healing. An abnormally high activity of PDGF is believed to play a central role in the etiology of certain adverse pathophysiological situations, such as atherosclerosis and restenosis [7, 8], as well as in other non-malignant diseases such as pulmonary fibrosis [9], glomerular nephritis [10], and rheumatoid arthritis [11]. Moreover, the PDGF B-chain was acquired as the sis oncogene by the acutely transforming simian sarcoma virus [12, 13]. The expression of a PDGF-like growth factor in cells infected with simian sarcoma virus or transfected with the sis oncogene leads to their transformation due to the persistent autocrine stimulation of the resident PDGF receptors.

Furthermore, certain human tumors possess PDGF receptors and express the genes for PDGF which suggest that autocrine growth stimulation via PDGF receptors contributes to the malignant phenotype of these tumors [2, 14].

The fact that PDGF is likely to be involved in the development of certain disorders has prompted the search for agents to block the action of PDGF. The approaches for interference with PDGF-induced signalling include peptides competing with PDGF for receptor binding [15], dominant negative mutants of PDGF [16, 17] or of PDGF receptor [18], and low molecular weight blockers of the receptor tyrosine kinase activity known as tyrphostins [19, PCT/US98/16232].

Certain tyrphostins which block PDGF-dependent proliferation of rabbit vascular smooth muscle cells [20] and of human bone marrow fibroblasts [21] have already been reported.

A novel class of tyrosine kinase blockers represented by the tyrphostins AG1295 and AG1296 was described by Kovalenko et al. [22]. These compounds inhibit selectively the platelet-derived growth factor (PDGF) receptor kinase and the PDGF dependent DNA synthesis in Swiss 3T3 cells and in porcine aorta endothelial cells (EC) with 50% inhibitory concentrations below 5 and 1 $\mu$M, respectively. These PDGF receptor blockers have no effect on epidermal growth factor receptor autophosphorylation, weak effects on DNA synthesis stimulated by insulin, by epidermal growth factor, or by a combination of both and over an order of magnitude weaker blocking effect on fibroblast growth factor-dependent DNA synthesis.

AG1296 potently inhibits signalling of human PDGF α- and β-receptors as well as of the related stem cell factor receptor (c-Kit) but has no effect on autophosphorylation of the vascular endothelial growth factor receptor KDR or on DNA synthesis induced by vascular endothelial growth factor in porcine aortic endothelial cells. Treatment by AG1296 reverses the transformed phenotype of sis-transfected NIH 3T3 cells but has no effect on src-transformed NIH 3T3 cells or on the activity of the kinase p60c-src(F527) immunoprecipitated from these cells [22].

In U.S. Pat. No. 5,932,580, further low molecular weight PDGF receptor kinase inhibitors, of the quinoxaline family, are described. Specifically, substituted analogs of 1,2-dimethyl-imidazolo[5,4-g]quinoxaline were shown to selectively inhibit PDGFR autophosphorylations and proliferation of PDGFR expressing cells, like porcine arterial smooth muscle cells (SMC), porcine endothelial cells and human internal mammary artery SMC, at $\mu$M concentration range.

The present invention describes enriched or purified geometrical isomers of compounds of the quinoxaline family known to be PDGF receptor kinase inhibitors, compositions including same, methods of their synthesis, purification and formulation and their use for treatment of proliferative malignant and non-malignant diseases or disorders, which show differential selectivity towards the PDGF receptor kinase. It is shown herein for the first time that geometrical isomers of compounds belonging to the quinoxaline are producable, isomerically purifyable and have differential affinity towards PDGF receptor kinase.

SUMMARY OF THE INVENTION

It is an object of the present invention to provided PDGF receptor kinase inhibitory compounds of the quinoxaline family, methods for their synthesis and purification and containment in, for example, slow release pharmaceutical compositions, and their use for treatment of a variety of diseases and disorders by local or systemic application.

According to one aspect of the present invention there is provided a preparation of a tyrphostin comprising a compound of a general formula:

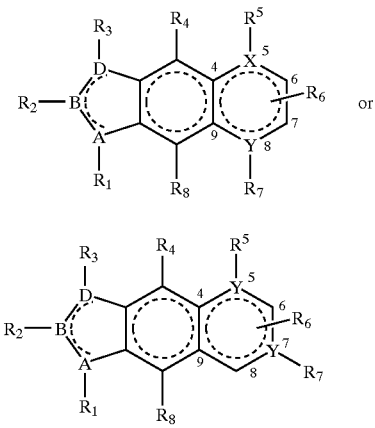

(Compound I)

(Compound II)

wherein, 4, 5, 6, 7, 8 and 9 indicate positions on a terminal 6-member ring;

A, B, D, X and Y are each independently selected from the group consisting of carbon, nitrogen, oxygen and sulfur;

$R_1$, $R_2$, $R_3$, $R_5$ and $R_7$ are each independently selected from the group consisting of hydrogen, alkyl, alkenyl, alkynyl, cycloalkyl, aryl, hydroxy, alkoxy, halo, C-carboxy, O-carboxy, carbonyl, thiocarbonyl, C-amido, guanly, sulfonyl, trihalomethane-sulfonyl and a pair of electrons, or alternatively, $R_1$ and $R_2$ or $R_2$ and $R_3$ form a 5-7 member ring structure;

$R_6$ is selected from the group consisting of alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, is halo, O-carbamyl, N-carbamyl, O-thiocarbamyl, N-thiocarbamyl, ureido, guanyl, guanidino, amino and a physiologically acceptable salt or a prodrug thereof;

$R_4$ and $R_8$ are each independently selected from the group consisting of hydrogen, alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and —$NR_{10}R_{11}$ and, a physiologically acceptable salt or a prodrug thereof;

$R_{10}$ and $R_{11}$ are each independently selected from the group consisting of hydrogen, alkyl, cycloalkyl, aryl, carbonyl and sulfonyl, or alternatively $R_{10}$ and $R_{11}$ form a five- or six-member heteroalicyclic ring; and, a physiologically acceptable salt or a prodrug thereof;

whereas, for Compound I, the preparation is enriched either for $R_6$ at position 6 or for $R_6$ at position 7, or, for Compound II, the preparation is enriched either for $R_6$ at position 6 or for $R_6$ at position 8.

According to further features in preferred embodiments of the invention described below, A, D, X and Y are each a nitrogen; B is a carbon; $R_1$ and $R_2$ are each independently selected from the group consisting of alkyl, alkoxy, halogen, nitro and amine group; $R_3$, $R_5$ and $R_7$ are each a pair of electrons; $R_6$ is an aryl, selected from the group consisting of phenyl, ferrocene, thiophene, furane, pyrrole, indole, thiazole, imidazole and pyridine.

According to still further features in the described preferred embodiments $R_1$ and $R_2$ are each a methyl; $R_4$ and $R_8$ are each a hydrogen.

According to still further features in the described preferred embodiments the preparation is enriched for Compound I in which $R_6$ is at position 6.

According to still further features in the described preferred embodiments the preparation is enriched for Compound I in which $R_6$ is at position 7.

According to still further features in the described preferred embodiments the preparation is enriched for Compound II in which $R_6$ is at position 6.

According to still further features in the described preferred embodiments the preparation is enriched for Compound II in which $R_6$ is at position 8.

According to still further features in the described preferred embodiments for Compound I, the preparation is purified either for $R_6$ at position 6 or for $R_6$ at position 7, or, for Compound II, the preparation is purified either for $R_6$ at position 6 or for $R_6$ at position 8.

According to another aspect of the present invention there is provided a pharmaceutical composition comprising, as an active ingredient, the preparation described herein and a pharmaceutically acceptable carrier.

According to further features in preferred embodiments of the invention described below, the pharmaceutically acceptable carrier is a slow release carrier.

According to still further features in the described preferred embodiments the slow release carrier is polylactic acid.

According to yet another aspect of the present invention there is provided a method of treating or preventing a protein tyrosine kinase related disorder in an organism, the method comprising the step of administering to the organism a therapeutically effective amount of the pharmaceutical composition described herein.

According to further features in preferred embodiments of the invention described below, the protein tyrosine kinase related disorder is selected from the group consisting of an EGF related disorder, a PDGF related disorder, an IGF related disorder and a met related disorder.

According to still further features in the described preferred embodiments the protein tyrosine kinase related disorder is selected from the group consisting of a cell proliferative disorder, a fibrotic disorder and a metabolic disorder.

According to still further features in the described preferred embodiments the cell proliferative disorder is selected from the group consisting of papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's disease, Burkitt's disease, arthritis, rheumatoid arthritis, diabetic retinopathy, angiogenesis, restenosis, in-stent restenosis, vascular graft restenosis.

According to still further features in the described preferred embodiments the cell fibrotic disorder is selected from the group consisting of pulmonary fibrosis, hepatic cirrhosis, atherosclerosis, glomerulonephritis, diabetic nephropathy, thrombic microangiopathy syndromes, transplant rejection.

According to still further features in the described preferred embodiments the cell metabolic disorder is selected from the group consisting of psoriasis, diabetes, wound healing, inflammation, and neurodegenerative diseases.

According to still further features in the described preferred embodiments the organism is a mammal.

According to still further features in the described preferred embodiments the mammal is a human.

According to still another aspect of the present invention there is provided a method of locally treating or preventing a disorder of a tissue of an organism comprising the step of locally applying the pharmaceutical composition described herein onto the tissue.

According to further features in preferred embodiments of the invention described below, the tissue is selected from the group consisting of blood vessel, lung and skin.

According to an additional aspect of the present invention there is provided a method of inhibiting cell proliferation comprising the step of subjecting the cells to the tyrphostin preparation described herein.

According to further features in preferred embodiments of the invention described below, the cells are of an organism, whereas subjecting the cells to the preparation is effected in vivo or in vitro.

According to yet an additional aspect of the present invention there is provided a method of enriching a preparation of tyrphostins for a specific geometrical isomer, the method comprising the steps of (a) chromatographing the preparation through a matrix, thereby separating isomers in the preparation; (b) collecting at least one specific isomer. Optionally, the method further comprising the step of (c) crystallizing the at least one specific isomer.

According to still an additional aspect of the present invention there is provided a method for preparing a pharmaceutical composition for slow release of a tyrphostin comprising the steps of (a) providing an isomer-enriched tyrphostin preparation as described herein; (b) dissolving or dispersing a slow release carrier and the isomer-enriched tyrphostin preparation in an organic solvent for obtaining an organic solution containing the carrier and the isomer-enriched tyrphostin preparation; (c) adding the organic solution into an aqueous solution for obtaining an oil-in-water-type emulsion; and (d) evaporating the organic solvent from the oil-in-water-type emulsion for obtaining a colloidal suspension of particles containing the slow release carrier and the isomer-enriched tyrphostin preparation.

According to further features in preferred embodiments of the invention described below, the slow release carrier is polylactic acid.

According to a further aspect of the present invention there is provided a stent comprising a substantially tubular body, the body is made of a material designed for slow release of a tyrphostin preparation as described herein.

The present invention successfully addresses the shortcomings of the presently known configurations by providing new and potent tyrphostins and delivery system for treatment of a variety of disorders and diseases.

BRIEF DESCRIPTION OF THE DRAWINGS

The invention is herein described, by way of example only, with reference to the accompanying illustrations, wherein.

DESCRIPTION OF THE PREFERRED EMBODIMENTS

Figure 1:
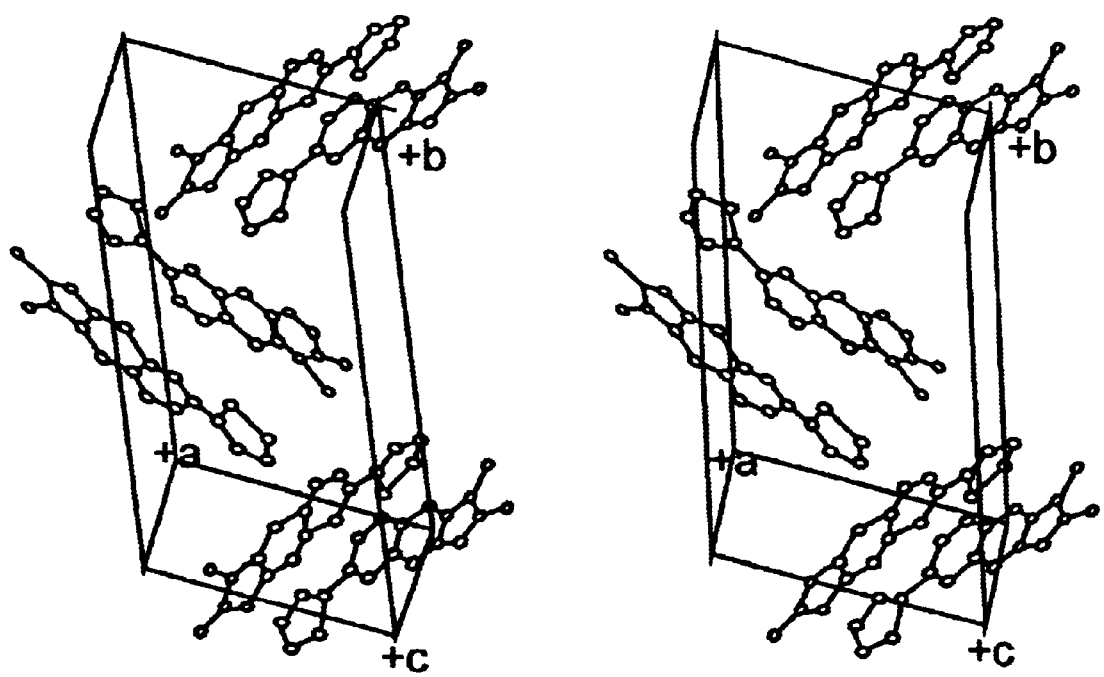
FIG. 1 shows two perspectives of a unit cell crystal structure of purified geometrical isomer AG2043 (1,2-dimethyl-6-(2-thiophene)imidazolo[5,4-g] quinoxaline)

The present invention is of quinoxaline derivatives, isomers of which modulate the activity of protein tyrosine kinases (PTKs). These may include disorders associated with tyrosine kinase receptors, such as, but not limited to, PDGFR, EGFR, IGFR, and FGFR. More specifically, the present invention is of enriched or purified geometrical isomers of compounds of the quinoxaline family known to be PDGF receptor kinase inhibitors, compositions including same, methods of their synthesis, purification and formulation and their use for treatment of proliferative malignant and non-malignant diseases, fibrotic or metabolic disorders, such as, but not limited to, psoriasis, hepatic cirrhosis, diabetes, atherosclerosis, restenosis, vascular graft restenosis, in-stent stenosis, angiogenesis, ocular diseases, pulmonary fibrosis, glomerular nephritis, and rheumatoid arthritis, and PDGF receptor associated malignancies, such as, but not limited to, leukemias and lymphomas, by local or systemic application of the disclosed preparations and compositions.

While conceiving the present invention, it was realized that the outcome of the chemical synthetic procedure of certain quinoxalines includes several isomeric products of the quinoxaline compound. More specifically, substitution on the terminal 6-member ring can assume two alternative positions. Thus, potential differences in specific isomer potency and selectivity were hypothesized, which may result in a differential blockade of PDGF receptor activation and consequent inhibition of, for example, SMC activation, migration and proliferation.

The experiments described below in the Examples section demonstrate that the two possible isomers are indeed formed, and are separable. Additionally, it is shown that tyrphostin-mediated inhibition of the PDGF receptor autophosphorylation results in the selective inhibition of SMC and PDGFR-expressing-PAEC cell proliferation and migration, in vitro, with a minimal inhibitory effect on KDR-expressing-PAEC cells. It is further shown below that the purified geometrical tyrphostin isomers AG2033 and AG2043 exhibit higher potency in completely blocking PDGF-BB induced phosphorylation of PDGF-β-R and consequent proliferation, relative to their isomeric counterparts, AG2034 and AG2044, respectively.

Tyrphostins-Containing-Preparations:

Thus, a preparation according to the present invention includes any mixture of synthetic tyrphostin products of the general formula:

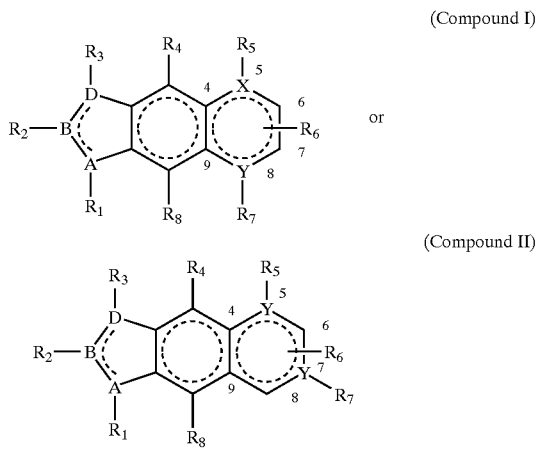

(Compound I)

(Compound II)

4, 5, 6, 7, 8 and 9 indicate positions on a terminal 6-member ring.

The doted lines indicate aromatic system.

A, B, D, X and Y are each independently a carbon, nitrogen, oxygen or sulfur.

$R_1, R_2, R_3, R_5$ and $R_7$ are each independently a hydrogen, alkyl, alkenyl, alkynyl, cycloalkyl, aryl, hydroxy, alkoxy, halo, C-carboxy, O-carboxy, carbonyl, thiocarbonyl, C-amido, guanly, sulfonyl, trihalomethane-sulfonyl and a pair of electrons, or alternatively, $R_1$ and $R_2$ or $R_2$ and $R_3$ form a 5-7 member ring structure.

$R_6$ is alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino or a physiologically acceptable salt or a prodrug thereof.

$R_4$ and $R_8$ are each independently hydrogen, alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and —$NR_{10}R_{11}$ and, a physiologically acceptable salt or a prodrug thereof.

$R_{10}$ and $R_{11}$ are each independently hydrogen, alkyl, cycloalkyl, aryl, carbonyl and sulfonyl, or alternatively $R_{10}$ and $R_{11}$ form a five- or six-member heteroalicyclic ring and, a physiologically acceptable salt or a prodrug thereof.

Additional examples for $R_6$ substituents are found in PCT/US98/16232, which is incorporated by reference, as if set forth herein (see Tables 1 and 2, on pages 20–27 and 34–35).

The preparation according to the present invention is enriched either for $R_6$ at position 6 or for $R_6$ at position 7 for Compound I, or the preparation is enriched either for $R_6$ at position 6 or for $R_6$ at position 8 for Compound II.

As used herein in the specification and in the claims section that follows, the term "prodrug" refers to an agent which is converted into an active parent drug in vivo. Prodrugs are often useful because in some instances they may be easier to administer than the parent drug. They may, for instance, be bioavailable by oral administration whereas the parent drug is not. The prodrug may also have improved solubility compared to the parent drug in pharmaceutical compositions. An example, without limitation, of a prodrug would be a compound of the present invention which is administered as an ester (the "prodrug") to facilitate transmittal across a cell membrane where water solubility is not beneficial, but which then is metabolically hydrolyzed to the carboxylic acid once inside the cell where water solubility is beneficial.

As used herein in the specification and in the claims section that follows, the term "ester" refers to a —C—OO—R" group, where R" is alkyl, cycloalkyl, aryl, heteroaryl (bonded through a ring carbon) or heteroalicyclic (bonded through a ring carbon).

As used herein in the specification and in the claims section that follows, the phrase "physiologically acceptable salt" refers to a charged species of the tyrphostin compound and its counter ion, so that it does not cause significant irritation to an organism and does not abrogate the biological activity and properties of the administered compound.

As used herein in the specification and in the claims section that follows, the phrase "enriched isomer preparation" refers to a preparation in which one isomer is represented in a higher proportion as compared to its synthesis proportion.

As used herein in the specification and in the claims section that follows, the term "alkyl" refers to a saturated aliphatic hydrocarbon including straight chain and branched chain groups. Preferably, the alkyl group has 1 to 20 carbon atoms. Whenever a numerical range; e.g., "1–20", is stated herein, it means that the group, in this case the alkyl group, may contain 1 carbon atom, 2 carbon atoms, 3 carbon atoms, etc., up to and including 20 carbon atoms. More preferably, it is a medium size alkyl having 1 to 10 carbon atoms. Most preferably, it is a lower alkyl having 1 to 4 carbon atoms. The alkyl group may be substituted or unsubstituted. When substituted, the substituent group can be, for example, cycloalkyl, aryl, heteroaryl, heteroalicyclic, hydroxy, alkoxy, aryloxy, thiohydroxy, thioalkoxy, thioaryloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or $NR_{10}R_{11}$, wherein $R_{10}$ and $R_{11}$ are each independently hydrogen, alkyl, cycloalkyl, aryl, carbonyl, sulfonyl, trihalomethysulfonyl and, combined, a five- or six-member heteroalicyclic ring.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamyl, N-carbamyl, C-amido, N-amido, nitro, amino and $NR_{10}R_{11}$ as defined above.

An "alkenyl" group refers to an alkyl group which consists of at least two carbon atoms and at least one carbon— carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $NR_{10}R_{11}$ as defined above.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino or $NR_{10}R_{11}$ as defined above.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and $NR_{10}R_{11}$ as defined above.

A "hydroxy" group refers to an —OH group.

An "azido" group refers to a —N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to an —SH group.

A "thioalkoxy" group refers to both an —S-alkyl group, and an —S-cycloalkyl group, as defined herein.

An "thioaryloxy" group refers to both an —S-aryl and an —S-heteroaryl group, as defined herein.

A "carbonyl" group refers to a —C(=O)—R" group, where R" is hydrogen, alkyl, cycloalkyl, aryl, heteroaryl (bonded through a ring carbon) or heteroalicyclic (bonded through a ring carbon) as defined herein.

An "aldehyde" group refers to a carbonyl group, where R" is hydrogen.

A "thiocarbonyl" group refers to a —C(=S)—R" group, where R" is as defined herein.

A "C-carboxy" group refers to a —C(=O)—O—R" groups, where R" is as defined herein.

An "O-carboxy" group refers to an R"C(=O)—O— group, where R" is as defined herein.

A "carboxylic acid" group refers to a C-carboxyl group in which R" is hydrogen.

A "halo" group refers to flourine, chlorine, bromine or iodine.

A "trihalomethyl" group refers to a —CX group wherein X is a halo group as defined herein.

A "trihalomethanesulfonyl" group refers to an $X_3CS(=O)_2$— group wherein X is a halo group as defined herein.

A "sulfinyl" group refers to an —S(=O)—R" group, where R" is as defined herein.

A "sulfonyl" group refers to an —S(=O)$_2$—R" group, where R" is as defined herein.

An "S-sulfonamido" group refers to a —S(=O)$_2$—$NR_{10}R_{11}$ group, with $R_{10}$ and $R_{11}$ as defined herein.

An "N-sulfonamido" group refers to an $R_{10}(=O)_2$—$NR_{11}$ group, where $R_{10}$ and $R_{11}$ are as defined herein.

A "trihalomethanesulfonamido" group refers to an $X_3CS(=O)_2NR_{10}$— group, where $R_{10}$ is as defined herein.

An "O-carbamyl" group refers to an —OC(=O)—$NR_{10}R_{11}$ group, where $R_{10}$ and $R_{11}$ are as defined herein.

An "N-carbamyl" group refers to an $R_{11}OC(=O)$—$NR_{10}$— group, where $R_{10}$ and $R_{11}$ are as defined herein.

An "O-thiocarbamyl" group refers to an —OC(=S)—$NR_{10}R_{11}$ group, where $R_{10}$ and $R_{11}$ are as defined herein.

An "N-thiocarbamyl" group refers to an $R_{11}OC(=S)NR_{10}$— group, where $R_{10}$ and $R_{11}$ are as defined herein.

An "Amino" group refers to an —$NH_2$ group.

A "C-amido" group refers to a —C(=O)—$NR_{10}R_{11}$ group, where $R_{10}$ and $R_{11}$ are as defined herein.

An "N-amido" group refers to an $R_{11}C(=O)$—$NR_{10}$ group, where $R_{10}$ and $R_{11}$ are as defined herein.

A "quaternary ammonium" group refers to an —$NHR_{10}R_{11}$ group, wherein $R_{10}$ and $R_{11}$ are independently alkyl, cycloalkyl, aryl or heteroaryl.

An "ureido" group refers to an —$NR_{10}C(=O)$—$NR_{11}R_{12}$ group, where $R_{10}$ and $R_{11}$ are as defined herein and $R_{12}$ is defined as either $R_{10}$ or $R_{11}$.

A "guanidino" group refers to an —$R_{10}NC(=N)$—$NR_{11}R_{12}$ group, where $R_{10}$, $R_{11}$ and $R_{12}$ are as defined herein.

A "guanyl" group refers to an $R_{10}R_{11}NC(=N)$— group, where $R_{10}$ and $R_{11}$ are as defined herein.

A "nitro" group refers to an —$NO_2$ group.

A "cyano" group refers to a —C≡N group.

A "silyl" group refers to a —Si(R")$_3$, where R" is as defined herein.

According to a preferred embodiment of the present invention A, D, X and Y are each a nitrogen. B is a carbon; $R_1$ and $R_2$ are each independently alkyl, alkoxy, halogen, nitro and amine group; $R_3$, $R_5$ and $R_7$ are each a pair of electrons and $R_6$ is an aryl such as phenyl, ferrocene, thiophene, furane, pyrrole, indole, thiazole, imidazole or pyridine.

According to a further preferred embodiment of the present invention wherein $R_1$ and $R_2$ are each a methyl, and $R_4$ and $R_8$ are each a hydrogen.

In any case, and as already mentioned, the preparation according to the present invention is enriched for $R_6$ at position 6 or at position 7 for Compound I. Alternatively, the preparation is enriched for $R_6$ at position 6 or at position 8 of Compound II.

According to a further preferred embodiment of the present invention the preparation is purified. Thus, for Compound I, the preparation is purified either for $R_6$ at position 6 or for $R_6$ at position 7, or, for Compound II, the preparation is purified either for $R_6$ at position 6 or for $R_6$ at position 8.

Herein the term "purified isomer preparation" refers to a preparation consisting of substantially 100% of a single isomer type.

Isomer Enrichment:

Further according to the present invention there is provided a method of enriching the preparation of tyrphostins for a specific geometrical isomer as herein described. The method includes the following steps:

First, the preparation is chromatographed through a matrix, thereby a separation of the different isomers is achieved.

Second, fractions from the chromatography are collected, such that at least one specific isomer is obtained.

Third, an optional step of crystallizing a specific isomer can be effected to achieve 100% purity in a crystal structure.

Pharmaceutical Compositions:

Further according to the present invention there is provided a pharmaceutical composition including a tyrphostin preparation as described hereinabove as an active ingredient. The preparation according to the present invention can be administered to an organism per se, or in a pharmaceutical composition where it is mixed with suitable carriers or excipients.

As used herein a "pharmaceutical composition" refers to a preparation of one or more of the isomeric compounds described herein, or physiologically acceptable salts or prodrugs thereof, with other chemical components such as physiologically suitable carriers and excipients. The purpose of a pharmaceutical composition is to facilitate administration of a compound to an organism.

Herein the term "active ingredient" refers to the tyrphostin preparation or compound accountable for the biological effect.

Hereinafter, the terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Routes of administration: Suitable routes of administration may, for example, include oral, rectal, transmucosal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a tyrphostin preparation in a local rather than systemic manner, for example, via injection of the preparation directly into a solid tumor often in a depot or slow release formulation, such as described below.

Furthermore, one may administer the drug in a targeted drug delivery system, for example, in a liposome coated with a tumor specific antibody. The liposomes will be targeted to and taken up selectively by the tumor.

Composition/formulation: Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The preparations described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The preparation of the present invention may also be formulated in rectal compositions such as suppositories or retention enemas, using, e.g., conventional suppository bases such as cocoa butter or other glycerides.

In addition to the formulations described previously, a preparation of the present invention may also be formulated for local administration, such as a depot preparation. Such long acting formulations may be administered by implantation (for example subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives such as sparingly soluble salts. Formulations for topical administration may include, but are not limited to, lotions, suspensions, ointments gels, creams, drops, liquids, sprays emulsions and powders.

According to a preferred embodiment of the present invention, the pharmaceutical composition is designed for a slow release of the tyrphostin preparation. The composition includes particles including a slow release carrier (typically, a polymeric carrier), such as, for example, polylactic acid, and the tyrphostin preparation. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein. The particles are preferably nanoparticles (i.e., in the nanometer range, e.g., in the range of about 1 to about 500 nm in diameter, preferably about 50–200 nm in diameter, most preferably about 100 nm in diameter).

Further according to the present invention there is provided a method of preparing a pharmaceutical composition for slow release of a tyrphostin.

The method includes the following steps:

First, an isomer-enriched tyrphostin preparation is provided, comprising of the above-described compounds.

Second, a slow release carrier (typically, a polymeric carrier) and the isomer-enriched tyrphostin preparation are dissolved or dispersed in an organic solvent for obtaining an organic solution containing the carrier and the isomer-enriched tyrphostin preparation;

Third, the organic solution is added into an aqueous solution for obtaining an oil-in-water-type emulsion. Preferably, the aqueous solution includes surface-active agent(s).

Fourth, the organic solvent is evaporated from the oil-in-water-type emulsion for obtaining a colloidal suspension of particles containing the slow release carrier and the isomer-enriched tyrphostin preparation.

According to a preferred embodiment of the present invention the slow release carrier is polylactic acid.

Further according to the present invention there is provided a stent, comprising a substantially tubular body, the body is made of or coated with a material designed for slow release of a tyrphostin preparation as described herein.

Specifically, a slow release formulation of the tyrphostin preparation can be used in patients undergoing balloon angioplasty, stent deployment, coronary artery bypass surgery, and heart transplantation as a preventive process of restenosis (see below, "The biochemistry").

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Many of the PTK modulating compounds in the claimed preparations of the present invention may be provided as physiologically acceptable salts wherein the compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate, etc, wherein the nitrogen of the quaternary ammonium group is a nitrogen of a compound of the present invention which reacts with an appropriate acid. Salts in which the compound forms the negatively charged species include, without limitation, the sodium, potassium, calcium and magnesium salts formed by the reaction of a carboxylic acid group in the molecule with the appropriate base (e.g., sodium hydroxide (NaOH), potassium hydroxide (KOH), calcium hydroxide (Ca(OH)$_2$), etc.).

Dosage: Pharmaceutical compositions suitable for use in context of the present invention include compositions wherein the active ingredients are contained in an amount effective to achieve the intended purpose. More specifically, a therapeutically effective amount means an amount of tyrphostin preparation effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from cell culture assays. For example, a dose can be formulated in animal models to achieve a circulating concentration range that includes the $IC_{50}$ as determined in cell culture (i.e., the concentration of the test compound, which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, termed the minimal effective concentration (MEC). The MEC will vary for each preparation, but can be estimated from in vitro data; e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10–90% of the time, preferable between 30–90% and most preferably 50–90%.

It is noted that, in the case of local administration or selective uptake, the effective local concentration of the drug may not be related to plasma concentration. In such cases, other procedures known in the art can be employed to determine the effective local concentration.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Packaging: Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes and the like.

The Biochemistry:

In yet another embodiment, the present invention relates to a method for the modulation of the catalytic activity of PTKs. The method is effected by administering a preparation of the present invention or a physiologically acceptable salt or prodrug thereof to a PTK.

By "PTK" is meant both receptor tyrosine kinases (RTKs) and cellular tyrosine kinases (CTKs or non-receptor TKs); i.e., the modulation of both RTK signal transduction and CTK signal transduction is contemplated by the present invention.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "modulation" refers to the alteration of the catalytic activity of RTKs and/or CTKs. In particular, modulation refers to the inhibition of the catalytic activity of RTKs and/or CTKs.

The term "catalytic activity" as used herein refers to the rate of phosphorylation of tyrosine under the influence, direct or indirect, of RTKs and/or CTKs.

The term "administering" as used herein refers to a method for bringing a tyrphostin preparation of the present invention and a target PK together in such a manner that the tyrphostin can affect the catalytic activity of the PK either directly; i.e., by interacting with the kinase itself or indirectly; i.e., by interacting with another molecule on which the catalytic activity of the kinase is dependent. As used herein, administration can be accomplished either in vitro, i.e. in a test tube, or in vivo, i.e., in cells or tissues of a living organism (see below).

A precise understanding of the mechanism by which the tyrphostin preparations of the present invention inhibits PTKs is not required in order to practice the present invention, however, while not being bound to any particular mechanism or theory, it is believed that tyrphostins interact with the amino acids of the catalytic region of PTKs. PTK typically possess a bi-lobate structure wherein ATP appears to bind in the cleft between the two lobes in a region where the amino acids are conserved among PTKs. Inhibitors of PTKs are believed to bind by non-covalent interactions such as hydrogen bonding, Van der Waals forces and ionic interactions in the same general region where the aforesaid ATP binds in the general space normally occupied by the adenine ring of ATP, i.e., PTK inhibitors are suggested to act as biomimetics to the ATP molecule. More specifically, it is thought that the quinoxaline ring component of tyrphostins binds in the general space normally occupied by the adenine ring of ATP. Recent studies have suggested that the profound selective PTK inhibition of such compounds results from competitive or mixed competitive interaction with the ATP binding domain as well as mixed competitive inhibition with substrate binding sub-sites [23]. Specificity of a particular quinoxaline for a particular PTK may arise as the result of additional interactions between the various substituents on the quinoxaline core and the amino acid domain specific to particular PTKs. Thus, the geometrical tyrphostin isomers of the present invention are formed during the synthetic procedure, which may have inherent differential capability to bind at the ATP binding domain, and hence selectivity towards certain PTK, such as PDGFR, and additional differential potencies at the specific PTK, e.g., PDGFR.

Further according to the present invention there is provided a method of inhibiting cell proliferation by subjecting the cells to a tyrphostin preparation of the compounds described hereinabove. In a preferred embodiment of the invention the cells are of an organism (e.g., a human), whereas subjecting the cells to the tyrphostin compound is effected in vivo. Alternatively, subjecting the cells to the tyrphostin compound is effected in vitro.

Thus, further according to the present invention there is provided a method of treating or preventing a protein tyrosine kinase related disorder or disease of an organism, such as a mammal (e.g., a human) by administering a therapeutically effective amount of the pharmaceutical composition as described above to the organism.

Herein, the term "treating" includes abrogating, substantially inhibiting, slowing or reversing the progression of a disease, substantially ameliorating clinical symptoms of a disease or substantially preventing the appearance of clinical symptoms of a disease.

Herein, the term "preventing" refers to a method for barring an organism from acquiring a disorder or disease in the first place.

As used herein, "PTK related disorder" refers to a disorder characterized by inappropriate PTK activity or overactivity of the PTK. Inappropriate activity refers to either; (i) PTK expression in cells which normally do not express PTKs; (ii) increased PTK expression leading to unwanted cell proliferation, differentiation and/or growth; or, (iii) decreased PTK expression leading to unwanted reductions in cell proliferation, differentiation and/or growth. Overactivity of PTKs refers to either amplification of the gene encoding a particular PTK or production of a level of PTK activity which can correlate with a cell proliferation, differentiation and/or growth disorder (that is, as the level of the PTK increases, the severity of one or more of the symptoms of the cellular disorder increases). Over activity can also be the result of ligand independent or constitutive activation as a result of mutations such as deletions of a fragment of a PTK responsible for ligand binding.

Thus, the PTK mediated disorders which are the object of the present invention can be studied, prevented or treated by the methods set forth herein whether the cells or tissues of the organism exist within the organism or outside the organism. Cells existing outside the organism can be maintained or grown in cell culture dishes. In this context, the ability of a particular compound to affect a PTK related disorder can be determined, e.g., the $IC_{50}$ of the compound can be ascertained before the use of the compounds in more complex living organisms is attempted. For cells outside the organism, multiple methods exist, and are well known to those skilled in the art, to administer compounds including, but not limited to, direct cell microinjection and numerous transmembrane carrier techniques. For cells harbored within a living organism, myriad methods also exist, and are likewise well-known to those skilled in the art, to administer compounds including, but not limited to, oral, parenteral, dermal and aerosol applications.

The term "organism" refers to any living entity comprised of at least one cell. A living organism can be as simple as, for example, a single eukaryotic cell or as complex as a mammal, including a human being.

The term "therapeutically effective amount" refers to that amount of the compound being administered which will relieve to some extent one or more of the symptoms of the disorder being treated.

The present invention is thus directed to tyrphostins-containing-preparations, which modulate PTK activity signal transduction by affecting the enzymatic activity of the RTKs and CTKs and thereby interfering with the signal transduced, by such proteins.

Examples, without limitation, of the types of disorders related to unregulated PTK activity that the preparations described herein may be useful in preventing, treating and studying are fibrotic disorders, metabolic disorders and cell proliferative disorders, related to PTKs such as PDGF, EGF, IGF and met.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombic microangiopathy syndromes, transplant rejection and glomerulopathies. In this regard, PDGFR has been implicated in the maintenance of mesangial cell proliferation. Other fibrotic disorders implicated include atherosclerosis.

The association between abnormal PTK activity and disease includes also metabolic diseases, such as psoriasis, diabetes mellitus, wound healing, inflammation and neurodegenerative diseases. For example, EGFR has been indicated in corneal and dermal wound healing. Defects in the Insulin-R and IGF-1R receptor are indicated in type-II diabetes mellitus.

Cell proliferative disorders which may be prevented, treated or further studied by the present invention include cancer, blood vessel proliferative disorders and mesangial cell proliferative disorders.

As used herein, the term "cancer" refers to various types of malignant neoplasms, most of which can invade surrounding tissues, and may metastasize to different sites, as defined by Stedman's medical Dictionary 25th edition (Hensyl ed., 1990). Examples of cancers which may be treated by the tyrphostins of the present invention include, but are not limited to, brain, ovarian, colon, prostate, kidney, bladder, breast, lung, oral and skin cancers which exhibit inappropriate PTK activity. These cancers can be further broken down. For example, brain cancers include glioblastoma multiforme, anaplastic astrocytoma, astrocytoma, ependyoma, oligodendroglioma, medulloblastoma, meningioma, sarcoma, hemangioblastoma, and pineal parenchymal. Likewise, skin cancers include melanoma and Kaposi's sarcoma. PTKs have been associated with the development of cancer. Some of the above mentioned PTK receptors, like EGFR and PDGFR, are over-expressed in many tumors and/or are persistently activated by autocrine loops have been demonstrated [31–33]. Specifically, PDGFR has been associated with glioblastoma, melanoma and lung, ovarian, and prostate cancer.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated. Of special relevance to the above described proliferative disorders are proliferation and migration processes involving activated smooth muscle cells (SMC), which are associated with release of abundant extracellular matrix by these cells, and are fundamental to neointimal growth associated with accelerated arteriosclerosis which continues to plague patients undergoing balloon angioplasty, stent deployment, coronary artery bypass surgery, and heart transplantation. Injury to the vessel wall, with or without loss or damage to the endothelium, causes a subpopulation of the quiescent, differentiated SMC to lose their contractile myofilamentary apparatus and transform into synthetic cells with large amounts of rough endoplasmic reticulum, ribosomes, and mitochondria. This transformation, directed, at least partially, by PDGF, is associated with SMC migration and proliferation followed by elaboration of abundant extracellular matrix. A variety of experimental studies have been directed toward the attenuation of SMC in vitro and in vivo. Nonetheless, relatively little progress has been made in the development of effective, selective, non-toxic inhibitors of SMC growth which might eventually be applied in the interventional setting. Recent progress in determining the mechanisms by which growth factors control cell proliferation has contributed to the development of treatment strategies which target specific signal transduction pathways in order to control proliferative disorders.

Specifically, inhibitors of protein tyrosine kinases (PTKs) have been shown to suppress SMC chemotaxis and proliferation. The tyrphostin phosphorylation inhibitors, which are at the center of the present invention, are low molecular weight, synthetic compounds whose basic structure can be modified to block specific receptor PTKs or intracellular PTKs. Unlike larger receptor antibodies, the small size of the tyrphostins permits easier access to receptor sites within tissues such as in the depths of the media. The development of this class of compounds was based on the concept that it would lead to a more focused control of proliferative disorders, achieve more improved therapeutic indices, and reduce the numerous untoward side effects of the more generalized inhibitors of DNA or RNA synthesis or cytoskeleton-disrupting agents. Indeed, it was recently shown that controlled local delivery of the non-selective PTK blocker AG17 (RG50872) effectively inhibits neointimal formation in a rat carotid balloon injury model [24].

The signal transduction induced by PDGF-BB, considered by many to be the strongest known mitogen and chemoattractant for arterial SMC, stimulates directed migration and proliferation of arterial SMC into the neointima following arterial injury. Platelet-derived growth factor (PDGF), expressed by platelets, SMC, endothelial cells, and macrophages, has been shown to play an important role in the pathogenesis of injury-induced neointimal formation in the arterial wall acting as both a mitogen and chemoattractant for SMC as well as being involved in the transformation of SMC from their contractile to the proliferative phenotype. In vivo studies have demonstrated that the expression of PDGF ligand and its receptor are elevated following arterial injury.

Infusion of PDGF into injured rat carotid arteries, or transfection of a plasmid coding for PDGF into porcine arteries, have also been shown to increase neointimal formation. PDGF receptor levels in SMC from human atherosclerotic plaques have also been reported to be elevated compared to receptor levels in normal medial SMC. Recently, Sirois et al. [25] have shown marked upregulation of PDGF receptors following injury to the vessel wall. They have demonstrated that the degree of neointimal formation substantially depends on both PDGFR-$\beta$ overexpression and its activation by PDGF-BB. They demonstrated further that controlled local delivery of antisense oligonucleotides to PDGF-$\beta$ receptor reduces neointimal formation in the rat carotid injury model. Finally, PTK blockers of the tyrphostin family have been shown to block PDGF receptor signal transduction, including the phosphorylation and activation of PLC$\gamma$, believed to be involved in SMC migration [20, 21, 22, 26].

Thus, further according to the present invention there is provided a method of locally treating a proliferative disorder of a tissue (e.g., an artery) of an organism (e.g., human) by applying a slow release pharmaceutical composition as described above onto the tissue. The disorder may be of any type above mentioned. More specifically, a disorder may be a proliferative disorder, associated with excessive or uncontrolled cell proliferation, including, but not limited to, psoriasis, papilloma, restenosis, atherosclerosis, in-stent stenosis, vascular graft restenosis, pulmonary fibrosis, glomerular nephritis, rheumatoid arthritis and PDGF receptor associated malignancies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion. The following protocols and experimental details are referenced in the Examples that follow:

Chemical Synthesis of Tyrphostins, Their Analysis and Structure Verification:

Synthesis of 1,2-dimethyl 5,6-diamino benzimidazole: This compound served as the starting material to the synthesis of all tyrphostins compounds as further detailed hereinunder. Synthesis of 1,2-dimethyl 5,6-diamino benzimidazole included the following synthesis steps:

Synthesis of 2-methyl benzimidazole: Phenylene diamine (32 grams) and glacial acetic acid (60 ml) were refluxed for 2 hours. Ice and KOH were added to bring the pH to 8.0, and the resulting light violet solid was filtered and collected.

Recrystallization from benzene yielded 30 grams of 2-methyl benzimidazole as a light yellow solid having a melting point of 170° C. and total yield of 77%.

Synthesis of 1,2-dimethyl benzimidazole: To 10 grams of 2-methyl benzimidazole (75 mM), crushed 25 grams of crushed KOH (450 mM) in 300 ml acetone, methyl iodide (15 grams, 105 mM) was added at a continuous drip for 0.5 hours, at room temperature. Following additional 0.5 hour, water was added, the reaction extracted with dichloromethane, evaporated and chromatographed on silica gel to yield 6 grams (54%) of 1,2-dimethyl benzimidazole as a white solid having a melting point of 102° C.

Synthesis of 1,2-dimethyl 5,6-dinitro Benzimidazole:

1,2-dimethyl benzimidazole (3.3 grams) in 15 ml $HNO_3$ (70%) was cooled with ice and 10 ml concentrated sulfuric acid was slowly added thereto. The reaction was then stirred at 100° C. for 2 hours, poured on ice and neutralized with KOH. Filtering resulted in 4 grams, 93% yield, of pale blue-white solid. The solid consisted of about 80% 1:1 mixture of 5-nitro:6-nitro; about 10% 4-nitro; and about 10% 5,6-dinitro isomers.

The above mixture (1.5 grams) was treated with 10 ml $HNO_3$ (70%) and 6 ml concentrated sulfuric acid at 190° C. for 3.5 hours, poured on ice and neutralized with KOH. Filtering resulted in collection of a light green solid. Recrystallization of that solid from ethanol yielded 0.48 grams (26% yield) of pure 5,6-dinitro isomer which is a white solid having a melting point of 224° C., NMR $CDCl_3$ d 8.17(1H, s), 7.90(1H, s), 3.87(3H, s), 2.73 (3H, s).

Synthesis of 1,2-dimethyl 5,6-diamino Benzimidazole:

Pure 1,2-dimethyl 5,6-dinitro benzimidazole (0.7 grams) and 0.2 grams Pd/C in 20 ml ethanol and 20 ml glacial acetic acid were hydrogenated for 4 hours. Filtering and evaporating resulted in 0.5 grams, 95% yield of a white solid having a melting point of 212° C.

Synthesis of AG2033 and AG2034 (Which are Geometrical Isomers 1851 Which is Described in U.S. patent application Ser. No. 08/980,596):

1,2-dimethyl 5,6-diamino benzimidazole (0.5 grams, 2.8 mM) and 0.45 grams, 3 mM, phenyl glyoxal hydrate in 20 ml ethanol and 20 ml acetic acid were refluxed for 3 hours, neutralized with NaOH, extracted with $CH_2Cl_2$, evaporated and analytically separated by chromatography on silica gel (TLC). The isomer AG2033 migrates at $R_f$=0.6 (5:95 $CH_3OH:CH_2Cl_2$), while the isomer AG2034 migrates at $R_f$=0.5.

Preparative separation of the isomers was achieved by chromatography on 150 grams silica gel, 70–230 mesh. Elution was conducted with 1% methanol in $CH_2Cl_2$.

(i) AG2033: 1,2-dimethyl-6-phenyl imidazolo[5,4-g]quinoxaline ("transoid"). From first fractions —0.265 grams (32% yield), a light yellow solid having a melting point of 275° C. NMR ($CDCl_3$): 9.30(1H, s, $H_7$), 8.45(1H, s. $H_4$), 8.21(2H, m), 7.95(1H, s, $H_9$) 7.50(3H, m), 3.88(3H, s, N-methyl), 2.75(3H, s, 2-methyl).

(ii) AG2034: 1,2-dimethyl-7-phenyl imidazolo[5,4-g]quinoxaline ("cisoid"). From later fractions—0.265 grams (32% yield), a light yellow solid having a melting point of 218° C. NMR ($CDCl_3$): 9.32(1H, s, $H_7$), 8.42(1H, s. $H_4$), 8.21(2H, m), 8.0(1H, s, $H_9$), 7.50(3H, m), 3.88(3H, s, N-methyl), 2.75(3H, s, 2-methyl). MS m/e—(AG1851—mixture of AG2033, AG2034)—274($M^+$, 100%), 259(M-$CH_3$, 8%), 247(M-HCN, 11%), 144(M-phenyl-HCN-CN, 68%), 129(144-$CH_3$, 13), 123(15), 102(12), 88(14), 77(15).

Scheme 1 below illustrates the synthesis and structure of the two isomers, AG2033 and AG2034.

SCHEME 1

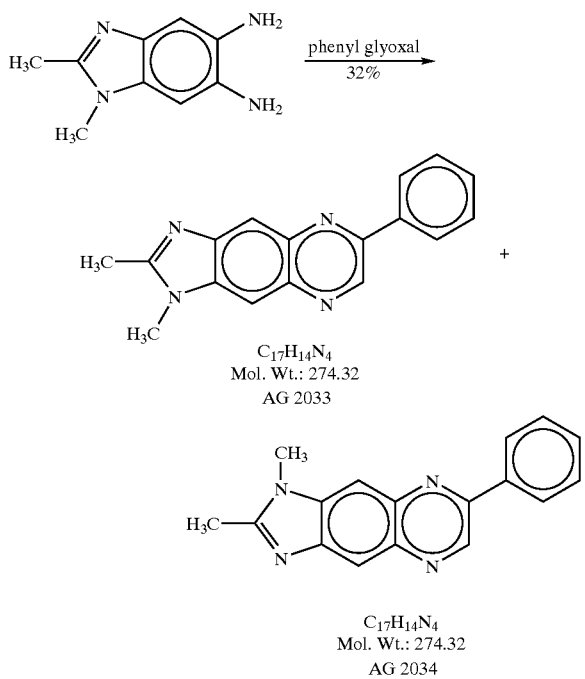

$C_{17}H_{14}N_4$
Mol. Wt.: 274.32
AG 2033

$C_{17}H_{14}N_4$
Mol. Wt.: 274.32
AG 2034

Synthesis of AG2043 and AG2044 (Which are Geometrical Isomers of AG1992 Which is Described in U.S. patent application No. 08/980,596):

4.6 grams, 20 mM, 1,2-dimethyl-5,6-dinitrobenzimidazole, hereinabove described, and 0.6 grams 5% Pd/C in 30 ml ethanol and 30 ml acetic acid were hydrogenated for 4 hours. After filtering 6.3 grams, 23 mM, thiophene glyoxal [34] and 1 ml HCl were added and the reaction refluxed for 1.5 hours, neutralized with KOH, extracted with $CH_2Cl_2$ and evaporated.

Preparative separation of the isomers was achieved by chromatography on 200 grams silica gel, 70–230 mesh. Elution was conducted with 1% methanol in $CH_2Cl_2$ resulting in:

(i) AG2043: 1,2-dimethyl-6-(2-thiophene) imidazolo[5,4-g]quinoxaline ("transoid"). From first fractions —0.23 grams (4% yield), a light yellow solid having a melting point of 274° C. Rf=0.6 (5:95 $CH_3OH:CH_2Cl_2$). NMR ($CDCl_3$): 9.20(1H, s, $H_7$), 8.34(1H, s. $H_4$), 7.87(1H, s, $H_9$), 7.83, 7.52, 7.20 (3H.ABX 12 line m, thiophene), 3.88 (3H, s, N-methyl), 2.75 (3H, s, 2-methyl). NMR (Acetone $d_6$): 9.38(1H, s, $H_7$), 8.12(1H, s. $H_4$), 8.02 (1H, s, $H_9$), 8.08, 7.71, 7.27 (3H.ABX 12 line m, thiophene), 3.97(3H, s, N-methyl), 2.70 (3H, s, 2-methyl). NMR (DMSO $d_6$): 9.48(1H, s, $H_7$), 8.15 (1H, s. $H_4$), 8.09(1H, s, $H_9$), 8.18, 7.81, 7.28 (3H.ABX 12 line m, thiophene), 3.88(3H, s, N-methyl), 2.66 (3H, s, 2-methyl). NMR (Nitrobenzene $d_5$): 9.0(1H, s, $H_7$), 8.01(1H, s. $H_4$), 7.60(1H, s, $H_9$), 7.61, 7.27, 6.92 (3H.ABX 12 line m, thiophene), 3.50(3H, s, N—$CH_3$), 2.38 (3H, s, 2—$CH_3$). MS m/e—(AG1992—mixture of AG2043, AG2044)—280 ($M^+$, 100%), 253(M-HCN, 8%), 144(M-thiophene-HCN—CN, 48%), 127(13), 111(11), 88(14), 76(9).

(ii) AG2044: 1,2-dimethyl-7-(2-thiophene) imidazolo[5,4-g]quinoxaline ("cisoid"). From following fractions—0.6 grams (11% yield), a light yellow solid having a melting point of 218° C. Rf=0.5 (5:95 CH$_3$OH:CH$_2$Cl$_2$). NMR (CDCl$_3$): 9.22(1H, s, H$_6$), 8.34(1H, s. H$_4$), 7.90(1H, s, H$_9$), 7.83, 7.52, 7.20 (3H.ABX 12 line m, thiophene), 3.88(3H, s, N-methyl), 2.75(3H, s, 2-methyl). NMR (Acetone d$_6$): 9.38(1H, s, H$_7$), 8.15(1H, s. H$_4$), 7.96(1H, s, H$_9$), 8.08, 7.71, 7.27 (3H.ABX 12 line m, thiophene), 3.97(3H, s, N-methyl), 2.70(3H, s, 2-methyl). NMR (DMSO d$_6$): 9.46(1H, s, H$_7$), 8.14(1H, s. H$_4$), 8.13(1H, s, H$_9$), 8.18, 7.81, 7.28 (3H.ABX 12 line m, thiophene), 3.88(3H, s, N-methyl), 2.66(3H, s, 2-methyl). NMR (Nitrobenzene d$_5$): 9.0 (1H, s, H$_7$), 8.05(1H, s. H$_4$), 7.47(1H, s, H$_9$), 7.64, 7.32, 6.95(3H.ABX 12 line m, thiophene), 3.50(3H, s, N-methyl), 2.38(3H, s, 2-methyl).

Scheme 2 below illustrates the synthesis and structure of the two isomers, AG2043 and AG2044.

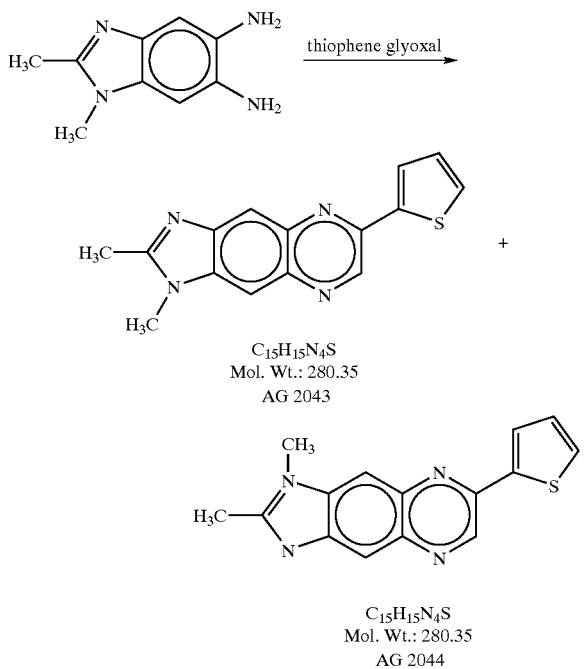

SCHEME 2

Cell Culture Techniques and Assays:
Cells and Reagents:

Smooth muscle cells (SMC) were obtained under aseptic conditions from porcine abdominal aortas. Each artery was cut open and the endothelial surface mechanically scraped. The vessels were then cut into 2 mm$^2$ fragments which were placed in culture dishes with Dulbecco's modified Eagle's medium (DMEM) supplemented with 15% (v/v) fetal calf serum (FCS), 100 u/ml penicillin, 100 μg/ml streptomycin, and 0.2 M L-glutamine. The tissue fragments were then placed in an incubator at 37° C. under 9% CO$_2$ atmosphere until SMC outgrowth was detected (typically within 3–7 days). Uniform populations of SMC which displayed the characteristic "hill and valley" growth pattern were subcultured using 0.25% trypsin for transfer. For experiments testing the effect of tyrphostins on growth inhibition and recovery (see below), SMC from passages 1–3 were replated in 15 mm wells pretreated with 3 μg/cm$^2$ fibronectin (Biological Industries, Kibbutz Beit Haemek, Israel) at 15,000 cells/well.

Porcine aortic endothelial cells (PAEC), stably transfected with either PDGF-receptor (PAEC/PDGFβR cells, kindly provided by Dr. L. Claesson-Welsh, Uppsala, Sweden) or VEGF-receptor KDR (PAEC/KDR), respectively, were used as previously described [27, 29]. Cells were routinely cultured in Ham's F-12 medium supplemented with geneticin (0.4 mg/ml) and 10% FCS.

Human coronary artery endothelial cells (HCAEC) and human coronary artery smooth muscle cells (HCASMC) were purchased from Clonetics (Heidelberg), and grown in EBM medium (supplemented with EGM-MV SINGLE QUOTS®) or in SmBM medium (supplemented with SmGM-2 SINGLE QUOTS®), respectively (Clonetics).

All cell culture reagents were from Gibco BRL, unless otherwise indicated. PDGF was the recombinant human BB homodimer. VEGF was obtained from Sigma. Anti-PDGF receptor antiserum DIG-1 was raised against a peptide corresponding to amino acid residues 1075–1089 in the human PDGF α-receptor which recognizes PDGF α- and β-receptors equally well [22]. Antiserum PDGF-R3 against PDGF receptor has been described [5]. [$^{32}$P]ATP was purchased from DuPont/N-EN (Dreieich, Germany). The polyclonal anti-KDR receptor antiserum NEF was raised against a synthetic peptide as previously described [28]. Additional reagents employed in specific experiments and their sources are indicated below.

In vitro effect of tyrphostins on purified PDGFR autophosphroylation: Membranes were prepared from confluent cultures of canine kidney epithelial cells (TRMP) or Swiss 3T3 cells as described [23]. Further purification of the PDGF-βR was performed as described in [23]. Briefly, 2 μl kinase preparation were incubated for 20 minutes on ice in the presence of 2 μg/ml PDGF-BB in 20 μl of 50 mM Hepes (pH 7.4). Kinase reaction was executed for 10 minute on ice with 5 mM MnCl$_2$, 1 mM vanadate, 10 μM [γ-$^{32}$P]ATP (2.5 μCi per reaction). The reaction was terminated by addition of 10 μl of a solution containing 6% SDS, 30% β-mercaptoethanol, 40% glycerol, and 0.5 mg/ml bromophenol blue. The samples were heated for 5 minutes at 95° C. and subjected to polyacrylamide gel electrophoresis in the presence of 0.4% SDS, using 7.5% polyacrylamide gels. The gels were stained, dried and subjected to autoradiographic analysis. For quantification of radioactivity in electrophoresis gels, a Phospho-Imager (Molecular Dynamics, Fuji, or Bio-Rad) was used according to the instructions of the manufacturer. To obtain autoradiograms, objects were exposed to X-ray film (Fuji RX or Kodak X-OMAT) with intensifying screens at -70° C.

Effect of tyrphostins on PDGF-induced PDGFR autophosphorylation in intact PAEC cells: PAEC cells, transfected with either PDGFR or KDR, cultivated in Ham's F-12 medium supplemented with 10% fetal calf serum (FCS), were synchronized for 20 hours in a medium containing 0.01% BSA. Following preincubation with AG1295 (which served as a non-isomerable control, see reference 23), AG2033, AG2034, AG2043 or AG2044 for 15 minutes, and with Na$_3$VO$_4$ (100 μM) for 5 minutes, the cells were stimulated with PDGF-BB (50 ng/ml) or VEGF-A (50 ng/ml) for 10 minutes at 37° C. After stimulation, the cells were solubilized in Nonidet P-40 (1%) containing lysis buffer.

The analysis of PDGF β-receptor phosphorylation was performed as follows. Cell lysates were subjected to immunoprecipitation using the PDGF β-receptor specific antiserum R3 [5]. The precipitates were subjected to polyacrylamide (7.5%) gel electrophoresis in presence of sodium dodecyl sulfate (SDS-PAGE) and were thereafter blotted onto a nitrocellulose membrane (Hybond C-EXTRA, Amersham). Phosphorylated proteins were detected by immunoblotting using the horseradish-peroxidase conjugated phosphotyrosine antibodies PY20 and 4G10 (Upstate Biotechnology), followed by application of secondary horseradish-peroxidase conjugated goat-anti-mouse antibody and chemoluminescence-based detection (ECL, Amersham) and autoradiography.

The analysis of KDR receptor phosphorylation was performed as follows. Cell lysates were subjected to immunoprecipitation using the KDR specific antiserum [27]. The precipitates were subjected to polyacrylamide (7.5%) gel electrophoresis in presence of sodium dodecyl sulfate (SDS-PAGE) and were thereafter blotted onto a nitrocellulose membrane (Hybond C-EXTRA, Amersham). Phosphorylated proteins were detected by immunoblotting using the horseradish-peroxidase conjugated phosphotyrosine antibody RC20H (Transduction Laboratories), followed by chemoluminescence-based detection (ECL, Amersham) and autoradiography.

Detection of receptor proteins was performed as follows. Cell lysates were subjected to immunoprecipitation using the PDGF β-receptor specific antiserum R3 or the KDR specific antiserum, as described above, and the precipitates washed three times and thereafter subjected to SDS-PAGE (7.5%) and blotting onto a nitrocellulose membrane (Hybond C-EXTRA, Amersham). Receptor proteins were detected by immunoblotting using the horseradish-peroxidase conjugated donkey anti-rabbit antibody (Amersham), followed by chemoluminescence-based detection (ECL, Amersham) and autoradiography.

Inhibition of cell proliferation and recovery: Monolayer cell growth inhibition and recovery experiments were repeated 3 or 4 times. Each experiment was performed in triplicate. Approximately 15,000 cells (SMC or PAEC) in 1 ml of culture medium supplemented with either 15% FCS (SMC) or 10% FCS (PAEC) were seeded on day 0 in 15 mm-wells precoated with fibronectin (SMC) or uncoated (PAEC). Cultures were treated with 10 $\mu$M of the following tyrphostin compounds: AG2033, AC2034, AG2043 and AG2044 (for SMC) or AG2033 (for PAEC) dissolved in 0.1% DMSO on days 1 and 3. On day 7, cultures were washed and the cells allowed to recover. Typically cells were counted on days 3 and 6 for inhibition, and on day 13 for recovery. The medium supplemented with serum (DMEM for SMC and Ham's F12 for PAEC) was changed every other day throughout the experiment.

Assessment of cell migration (Chemotaxis assay): The chemotactic response of HCASMC, PAEC/KDR and PAEC/PDGFR cells was assessed using the modified Boyden chamber (Neuro Probe, Inc.) and collagen-coated polycarbonate filters (Nucleopore) with pore diameters of 8 $\mu$m as previously described [27]. Briefly, PAEC/KDR and PAEC/PDGFR cells were cultivated and assayed in Ham's F12 medium containing 10% FCS. HCASMC were cultivated in SmGM-2 (clonetics) and assayed in SmBM-WM containing 10% FCS and 0.1% BSA. To the medium in the lower part of the Boyden chamber, either VEGF or PDGF-BB (10 ng/ml, respectively) were added. AG2033 was added to both upper and lower chamber parts. Suspended cells were given 4 hours for migration, after a preincubation period of 15 minute in AG2033. The number of cells that migrated without PDGF-BB or VEGF stimulation was referred to as 100% migration (chemokinesis). The assay was performed in triplicate, and five medium-power fields were counted per well using a light microscope (Jenalab).

Assessment of cell proliferation ([$^3$H]thymidine incorporation assay): PAEC/KDR and PAEC/PDGFR cells, grown in Ham's F12 medium containing 10% FCS were seeded sparsely in 12 well culture dishes. After 24 hours, cells were washed two times with Ham's F12 medium containing 1% FCS and incubated for additional 48 hours with one renewal of medium. Cells were incubated for 15 minute with different concentrations of AG2033 (0.1; 1 and 10 $\mu$M) or with the solvent DMSO alone, stimulated with 3 ng/ml VEGF or with 15 ng/ml PDGF-BB for 20 hours, followed by addition of 0.25 $\mu$Ci of [$^3$H]-thymidine/ml (Amersham) for two hours. High molecular weight [$^3$H]-radioactivity was precipitated using 5% trichloroacetic acid at 4° C. for 30 minutes. After two washes with ice-cold $H_2O$, [$^3$H]-radioactivity was solubilized in 1 M NaOH (400 $\mu$l/well) at room temperature for 8 minutes, neutralized by the addition of 2 M HCL (400 $\mu$l/well), and quantitated by liquid scintillation counting.

Experimental Results

Example 1

Chemical Analysis

X-ray Crystal Structure Analysis:

AG2043:

All crystallographic computings were performed using a VAX9000 computer at the Hebrew University of Jerusalem, employing the TEXSAN Structure Analysis Software. Data were acquired using an ENRAF-NONIUS CAD-4 Computer-Controlled Diffractometer. $CuK_\alpha (\lambda=1.54178$ Å) radiation with a graphite crystal monochromator in the incident beam was used. The standard CAD-4 centering, indexing, and data collection programs were used. The unit cell dimensions were obtained by a least-squares fit of 20 centered reflections in the range of $23° \leq \theta \leq 27°$.

Intensity data were collected using the $\omega$-2$\theta$ technique to a maximum 2$\theta$ of 120°. The scan width, $\Delta\omega$, for each reflection was 0.80±0.15 tan $\theta$. An aperture with a height of 4 mm and a variable width, calculated as 2.0±0.5 tan $\theta$ mm, was located 173 mm from the crystal. Reflections were first measured with a scan of 8.24°/minute. The rate of the final scan was calculated from the preliminary scan results so that the ratio I/$\sigma$ (I) would be at least 40 but the maximum scan time would not exceed 60 seconds. If in the preliminary scan I/$\sigma$ (I)<2, this measurement was used as the datum. Scan rates varied from 1.27 to 8.24°/minute. Of the 96 steps in the scan, the first and the last 16 steps were considered to be background. During data collection the intensities of three standard reflections were monitored after every hour of X-ray exposure. No decay was observed. In addition, three orientation standards were checked after 100 reflections to check for the effects of crystal movement. If the standard deviation of the h, k, and l values of any orientation reflection exceeded 0.08, a new orientation matrix was calculated on the basis of the recentering of the 20 reference reflections.

Intensities were corrected for Lorentz and polarization effects. All non-hydrogen atoms were found by using the results of the SHELX-86 direct method analysis (30). After several cycles of refinements, the positions of the hydrogen atoms were calculated, and added to the refinement process. Refinement proceeded to convergence by minimizing the function $\Sigma w(|F_o|-|F_c|)^2$. A final difference Fourier synthesis map showed several peaks less than 0.31 e/Å$^3$ scattered about the unit cell without a significant feature.

Table 1 below presents the discrepancy indices, $R=\Sigma||F_o|-|F_c||/\Sigma|F_o|$ and $R_w=[\Sigma w(|F_o|-|F_c|)^2/\Sigma w|F_o|^2]^{1/2}$ as well as other pertinent crystallographic data, obtained for the AG2043 pure isomer crystal.

TABLE 1

Crystallographic data for AG2043

| | |
|---|---|
| Formula | $C_{15}H_{12}N_4S$ |
| Space group | $P2_1$ |
| a, Å | 10.834 (2) |
| b, Å | 19.081 (4) |
| c, Å | 6.618 (1) |
| β, deg | 107.10 (1) |
| V, Å$^3$ | 1307.7 (5) |
| Z | 4 |
| ρcalc., gcm$^{-3}$ | 1.42 |
| μ (CuK$_\alpha$), cm$^{-1}$ | 21.46 |
| No. of unique reflections | 2007 |
| No. of reflections with I ≧ 3σ$_I$ | 1688 |
| R | 0.049 |
| R$_w$ | 0.062 |

AG2044:

All crystallographic computings were performed using a VAX9000 computer at the Hebrew University of Jerusalem, employing the TEXSAN Structure Analysis Software. Data were acquired using an ENRAF-NONIUS CAD-4 Computer-Controlled Diffractometer. CuK$_\alpha$(λ=1.54178 Å) radiation with a graphite crystal monochromator in the incident beam was used. The standard CAD-4 centering, indexing, and data collection programs were used. The unit cell dimensions were obtained by a least-squares fit of 24 centered reflections in the range of 25°≦θ≦30°.

Intensity data were collected using the ω-2θ technique to a maximum 2θ of 120°. The scan width, Δω, for each reflection was 0.80±0.15 tan θ. An aperture with a height of 4 mm and a variable width, calculated as 2.0+0.5 tan θ mm, was located 173 mm from the crystal. Reflections were first measured with a scan of 8.24°/minute. The rate of the final scan was calculated from the preliminary scan results so that the ratio I/σ (I) would be at least 40 but the maximum scan time would not exceed 60 seconds. If in the preliminary scan I//σ (I)<2, this measurement was used as the datum. Scan rates varied from 1.27 to 8.24°/minute. Of the 96 steps in the scan, the first and the last 16 steps were considered to be background. During data collection the intensities of three standard reflections were monitored after every hour of X-ray exposure. No decay was observed. In addition, three orientation standards were checked after 100 reflections to check the effects of crystal movement. If the standard deviation of the h, k, and l values of any orientation reflection exceeded 0.08, a new orientation matrix was calculated on the basis of the recentering of the 24 reference reflections.

Intensities were corrected for Lorentz and polarization effects. All non-hydrogen atoms were found by using the results of the SHELX-86 direct method analysis (30). After several cycles of refinements the positions of the hydrogen atoms were calculated, and added to the refinement process. Refinement proceeded to convergence by minimizing the function $\Sigma w(|F_o|-|F_c|)^2$. A final difference Fourier synthesis map showed several peaks less than 0.37 e/Å$^3$ scattered about the unit cell without a significant feature.

Table 2 below presents the discrepancy indices, $R=\Sigma||F_o|-|F_c||/\Sigma|F_o|$ and $R_w=[\Sigma w(|F_o|-|F_c|)^2/\Sigma wF_o^2]^{1/2}$, as well as other pertinent crystallographic data, obtained for the AG2044 pure isomer crystal.

TABLE 2

Crystallographic data for AG2044

| | |
|---|---|
| Formula | $C_{15}H_{12}N_4S$ 1.5H$_2$O |
| Space group | $P2_1/c$ |
| a, Å | 7.261 (3) |
| b, Å | 17.789 (3) |
| c, Å | 23.293 (4) |
| β, deg | 98.00 (3) |
| V, Å$^3$ | 2979 (1) |
| Z | 8 |
| ρcalc., gcm$^{-3}$ | 1.37 |
| μ (CuK$_\alpha$), cm$^{-1}$ | 20.07 |
| No. of unique reflections | 4560 |
| No. of reflections with I ≧ 3σ$_I$ | 3621 |
| R | 0.051 |
| R$_w$ | 0.074 |

Crystallization of AG2043 and AG2044 from acetonitrile gave single crystals, whose structures were unequivocally determined by X-ray analysis. The unit cell of AG2043 and AG2044 contained two different orientations of each molecule (as shown in the unit cells presented in FIGS. 1 and 3), with water molecule in the unit cell of AG2044.

Tables 3 and 4 below present further data characterizing the crystal structure of AG2043, providing intramolecular bond distances (Table 3) and angles parameters (Table 4) involving the nonhydrogen atoms. Tables 5, 6, 7 below present further data characterizing the crystal structure of AG2044, providing intramolecular bond distances (Table 5), intramolecular angles (Table 6) and intermolecular distances involving the nonhydrogen atoms (Table 7).

Figure 2A:
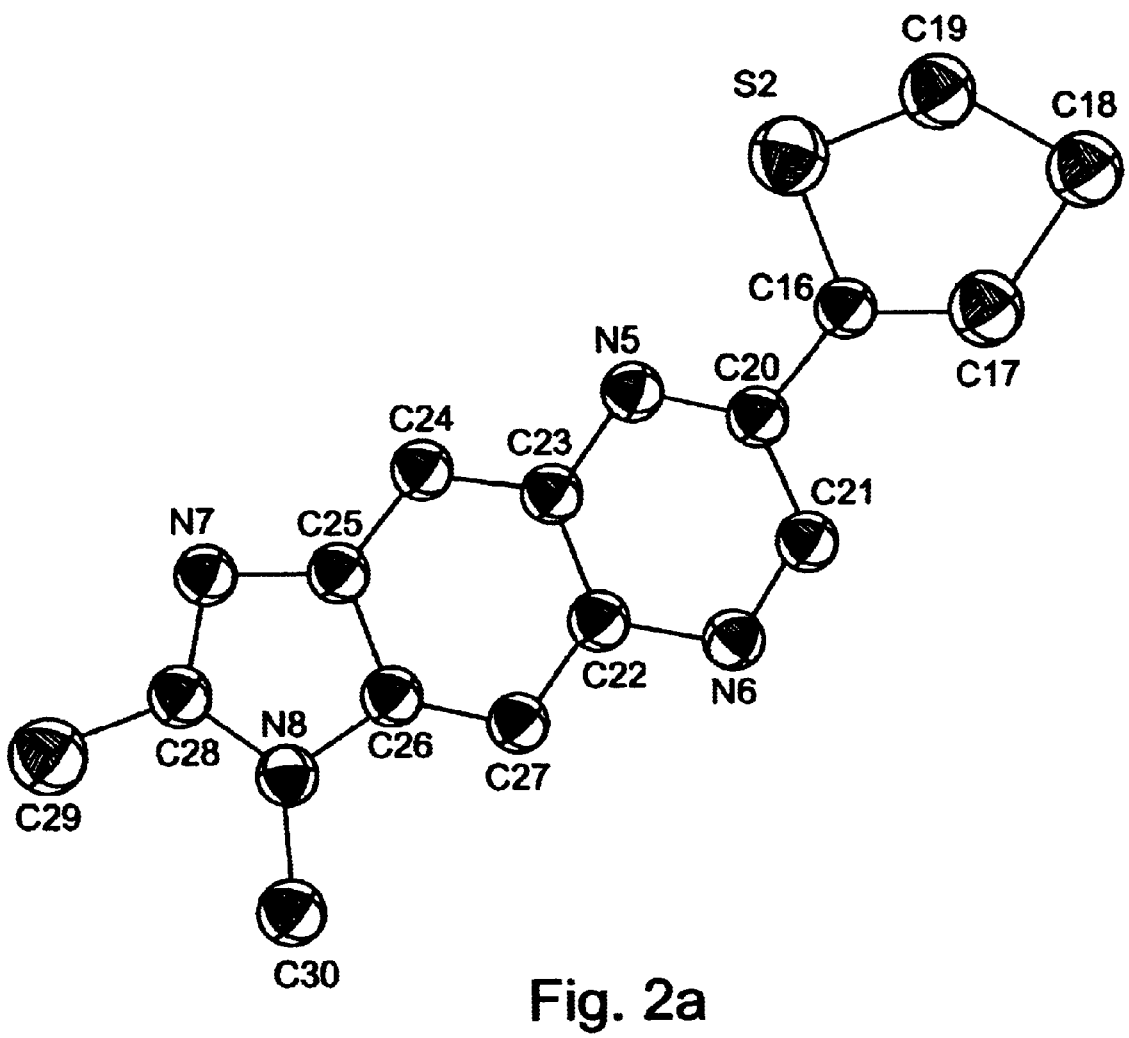
FIGS. 2a–b show the molecular structure of geometrical isomer AG2043 (1,2-dimethyl-6-(2-thiophene)imidazolo[5,4-g] quinoxaline) according to the present invention.
Figure 2B:
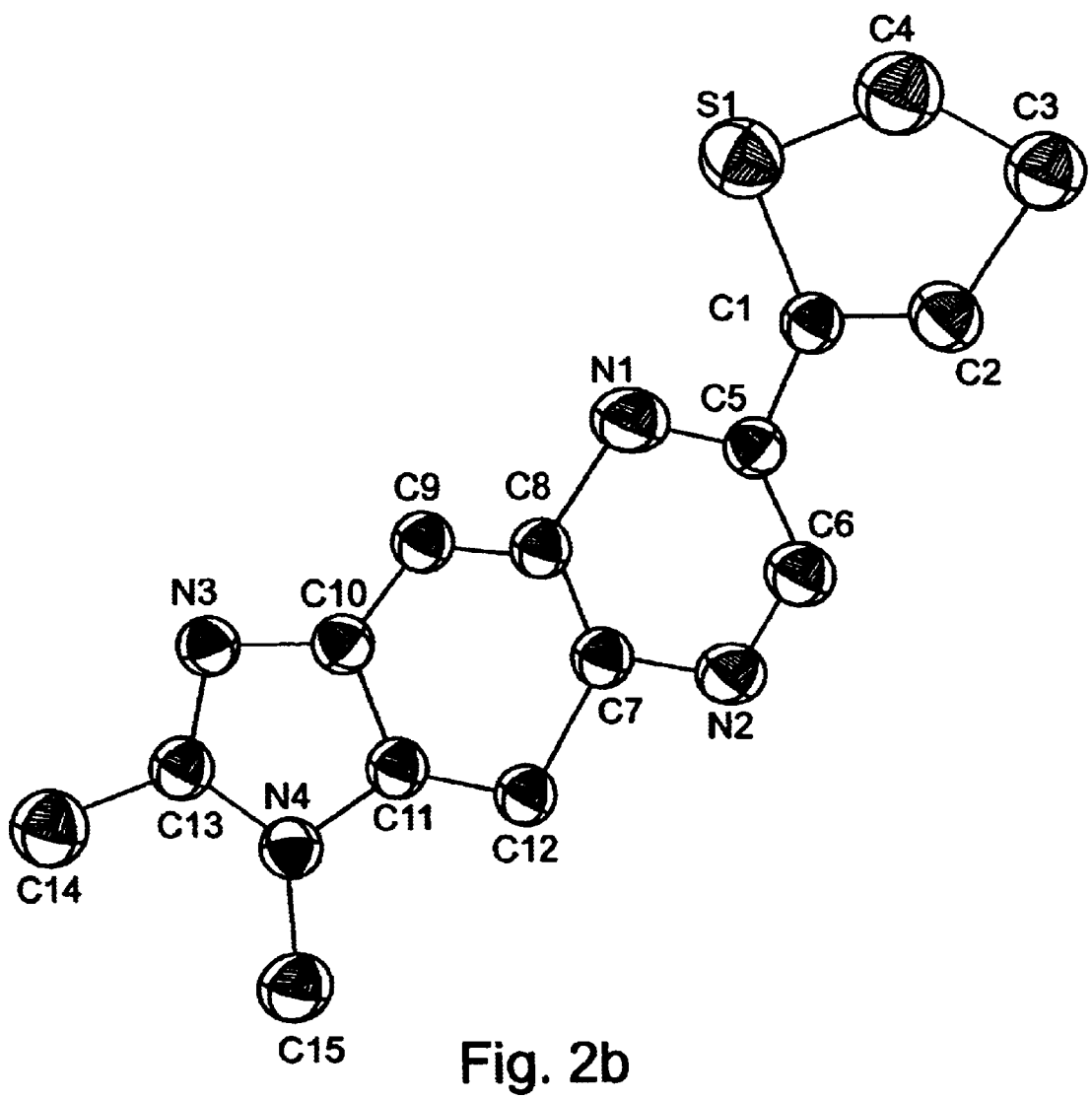

FIGS. 1, 2a–b present the unit cell crystal structure of AG2043, as obtained following crystallization from acetonitrile by X-ray analysis (FIG. 1), as well as the molecular structure of AG2043 (FIGS. 2a–b).

Figure 3:
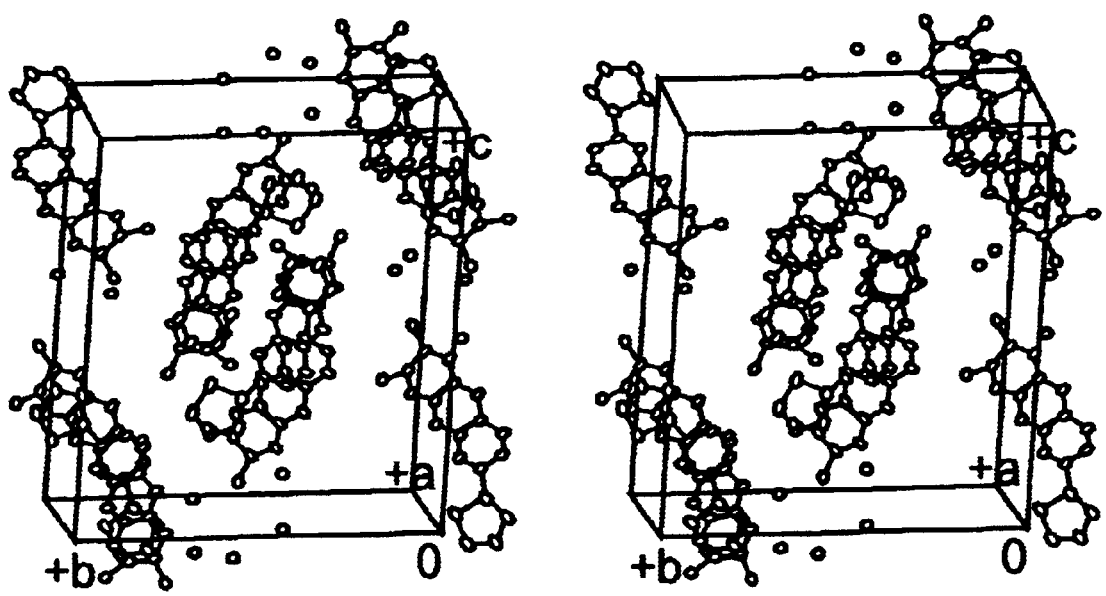
FIG. 3 shows two perspectives of a unit cell crystal structure of purified geometrical isomer AG2044 (1,2-dimethyl-7-(2-thiophene)imidazolo[5,4-g] quinoxaline)
Figure 4A:
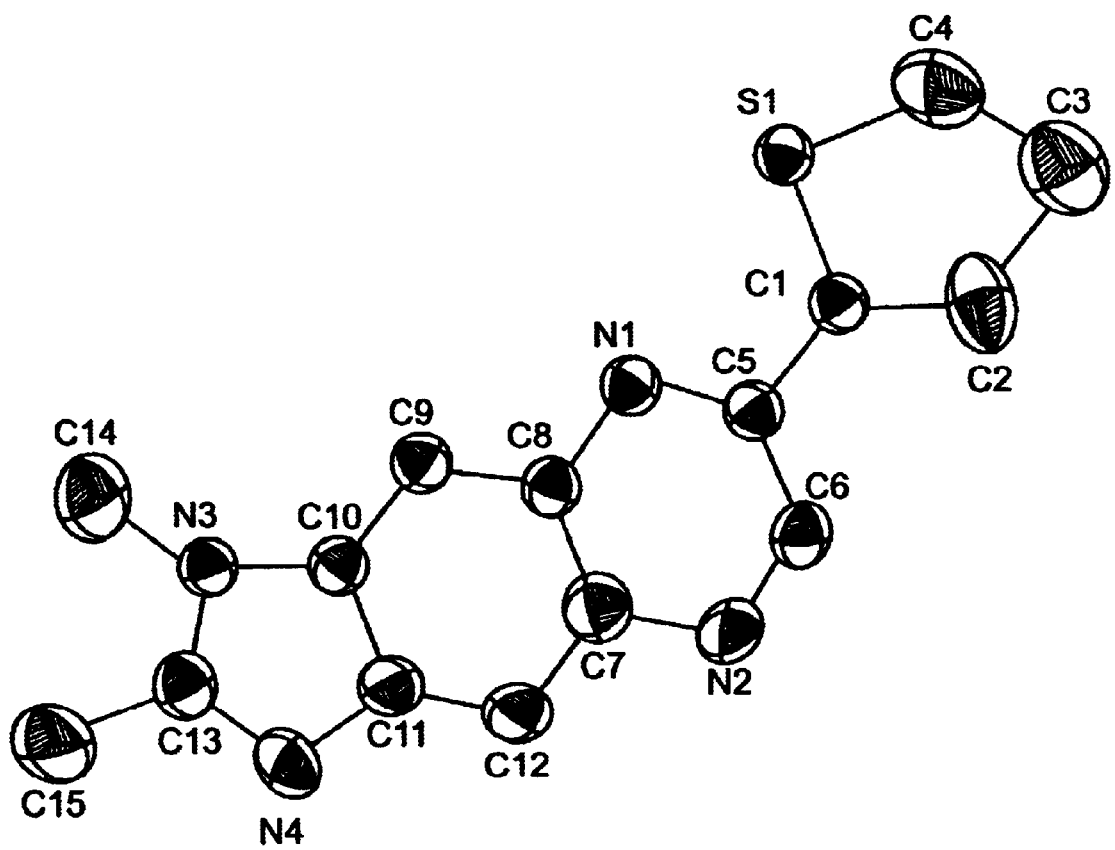
FIGS. 4a–b show the molecular structure of geometrical isomer AG2044 (1,2-dimethyl-7-(2-thiophene)imidazolo[5,4-g] quinoxaline) according to the present invention.
Figure 4B:
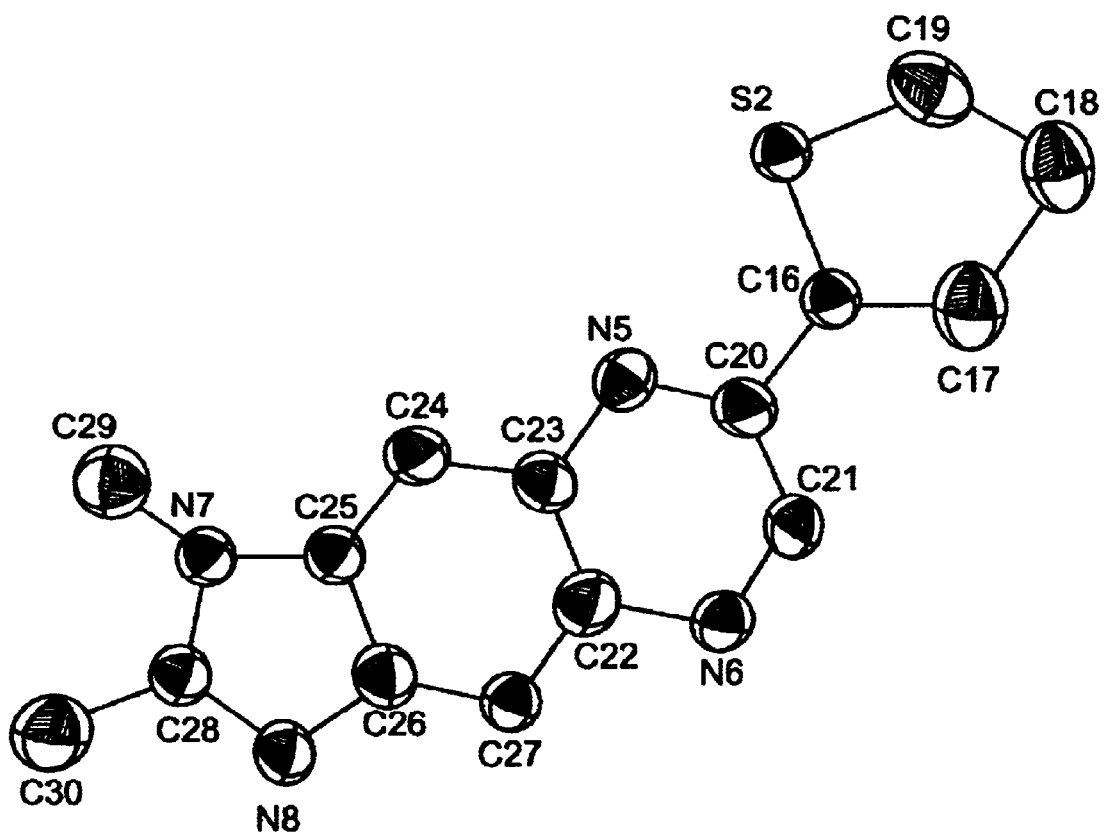

FIGS. 3, 4a–b present the unit cell crystal structure of AG2044, as obtained following crystallization from acetonitrile by X-ray analysis (FIG. 3), as well as the molecular structure of AG2044 (FIGS. 4a–b).

Molecular structure of the presented compounds may thus be divided according to their geometrical arrangement: similar to substituents on double bonded carbons, the substituents can either reside on the same side of the double bond (cis), or on opposing sides (trans). Thus, substituents on the nitrogens of the imidazole ring (terminal 5-member ring) at positions 1 and 2 can either reside on the same side as the aryl substituent in the terminal 6 member ring (position 7 of the compound), forming a "cis-like" geometrical arrangement ("cisoid"), or on opposing side (position 6 of the compound), forming a "trans-like" geometrical arrangement ("transoid").

The data shown herein proves the structure of the more potent isomer, AG2043, (see below, biological activity results), to be the "transoid" structure, i.e., 1,2-dimethyl-6-thiophene (FIGS. 2a–b), where the 1-Methyl and the thiophene ring are "trans" to each other, and AG2044 the "cisoid" structure, 1,2-dimethyl-7-thiophene analog (FIGS. 4a–b).

Turning to evaluate chemical and biological characteristics of the AG2033 and AG2034 isomers pair, similar results were obtained: migration rate on silica gel (TLC) yielded identical R$_f$'s (0.5 and 0.6 for AG2034 and AG2033, respectively) as well as NMR structure analysis. Additionally, evaluation of in vitro inhibition of PDGFβR autophosphorylation resulted in differential potencies of the compounds, proving AG2033 to be the more potent isomer compared to AG2034 (see biological results, below). Thus, by analogy to the AG2043 and AG2044 isomers pair, the pair of inhibitors AG2033 and AG2034 (in which a phenyl ring substitutes the thiophene) is assumed to have the "transoid" structure for AG2033.

TABLE 3

Intramolecular distances involving the nonhydrogen atoms AG2043

| atom | atom | distance | atom | atom | distance |
|---|---|---|---|---|---|
| S (1) | C (1) | 1.733 (6) | C (1) | C (5) | 1.454 (9) |
| S (1) | C (4) | 1.700 (8) | C (2) | C (3) | 1.41 (1) |
| S (2) | C (16) | 1.709 (6) | C (3) | C (4) | 1.33 (1) |
| S (2) | C (19) | 1.703 (9) | C (5) | C (6) | 1.420 (9) |
| N (1) | C (5) | 1.328 (7) | C (7) | C (8) | 1.430 (8) |
| N (1) | C (8) | 1.371 (7) | C (7) | C (12) | 1.396 (8) |
| N (2) | C (6) | 1.291 (8) | C (8) | C (9) | 1.405 (8) |
| N (2) | C (7) | 1.380 (7) | C (9) | C (10) | 1.383 (8) |
| N (3) | C (10) | 1.386 (8) | C (10) | C (11) | 1.425 (8) |
| N (3) | C (13) | 1.297 (8) | C (11) | C (12) | 1.363 (8) |
| N (4) | C (11) | 1.371 (7) | C (13) | C (14) | 1.471 (9) |
| N (4) | C (13) | 1.392 (7) | C (16) | C (17) | 1.359 (9) |

TABLE 3-continued

Intramolecular distances involving the nonhydrogen atoms AG2043

| atom | atom | distance | atom | atom | distance |
|---|---|---|---|---|---|
| N (4) | C (15) | 1.442 (8) | C (16) | C (20) | 1.469 (9) |
| N (5) | C (20) | 1.314 (8) | C (17) | C (18) | 1.44 (1) |
| N (5) | C (23) | 1.369 (8) | C (18) | C (19) | 1.31 (1) |
| N (6) | C (21) | 1.309 (8) | C (20) | C (21) | 1.410 (9) |
| N (6) | C (22) | 1.367 (7) | C (22) | C (23) | 1.447 (8) |
| N (7) | C (25) | 1.397 (8) | C (22) | C (27) | 1.386 (8) |
| N (7) | C (28) | 1.306 (8) | C (23) | C (24) | 1.383 (8) |
| N (8) | C (26) | 1.378 (8) | C (24) | C (25) | 1.375 (8) |
| N (8) | C (28) | 1.376 (8) | C (25) | C (26) | 1.417 (8) |
| N (8) | C (30) | 1.461 (8) | C (26) | C (27) | 1.372 (8) |
| C (1) | C (2) | 1.362 (9) | C (28) | C (29) | 1.48 (1) |

Distances are in angstroms. Estimated standard deviations in the least significant figure are given in parentheses.

TABLE 4

Intramolecular bond angles involving the nonhydrogen atoms AG2043

| atom | atom | atom | angle | atom | atom | atom | angle |
|---|---|---|---|---|---|---|---|
| C (1) | S (1) | C (4) | 91.3 (4) | C (8) | C (7) | C (12) | 121.2 (5) |
| C (16) | S (2) | C (19) | 91.3 (4) | N (1) | C (8) | C (7) | 120.8 (5) |
| C (5) | N (1) | C (8) | 117.1 (5) | N (1) | C (8) | C (9) | 118.0 (5) |
| C (6) | N (2) | C (7) | 117.0 (5) | C (7) | C (8) | C (9) | 121.1 (6) |
| C (10) | N (3) | C (13) | 106.1 (5) | C (8) | C (9) | C (10) | 117.1 (5) |
| C (11) | N (4) | C (13) | 107.0 (5) | N (3) | C (10) | C (9) | 130.2 (5) |
| C (11) | N (4) | C (15) | 125.8 (5) | N (3) | C (10) | C (11) | 109.4 (5) |
| C (13) | N (4) | C (15) | 127.2 (5) | C (9) | C (10) | C (11) | 120.4 (5) |
| C (20) | N (5) | C (23) | 117.8 (5) | N (4) | C (11) | C (10) | 104.9 (5) |
| C (21) | N (6) | C (22) | 116.9 (5) | N (4) | C (11) | C (12) | 131.5 (6) |
| C (25) | N (7) | C (28) | 105.0 (5) | C (10) | C (11) | C (12) | 123.5 (6) |
| C (26) | N (8) | C (28) | 107.1 (5) | C (7) | C (12) | C (11) | 116.6 (5) |
| C (26) | N (8) | C (30) | 125.1 (5) | N (3) | C (13) | N (4) | 112.6 (5) |
| C (28) | N (8) | C (30) | 127.8 (6) | N (3) | C (13) | C (14) | 126.1 (5) |
| S (1) | C (1) | C (2) | 110.3 (5) | N (4) | C (13) | C (14) | 121.3 (6) |
| S (1) | C (1) | C (5) | 119.2 (4) | S (2) | C (16) | C (17) | 111.7 (5) |
| C (2) | C (1) | C (5) | 130.4 (6) | S (2) | C (16) | C (20) | 120.2 (5) |
| C (1) | C (2) | C (3) | 112.7 (6) | C (17) | C (16) | C (20) | 128.1 (6) |
| C (2) | C (3) | C (4) | 113.1 (7) | C (16) | C (17) | C (18) | 111.3 (7) |
| S (1) | C (4) | C (3) | 112.5 (6) | C (17) | C (18) | C (19) | 112.6 (8) |
| N (1) | C (5) | C (1) | 117.6 (5) | S (2) | C (19) | C (18) | 113.1 (7) |
| N (1) | C (5) | C (6) | 121.0 (6) | N (5) | C (20) | C (16) | 117.4 (5) |
| C (1) | C (5) | C (6) | 121.3 (6) | N (5) | C (20) | C (21) | 121.2 (6) |
| N (2) | C (6) | C (5) | 123.9 (6) | C (16) | C (20) | C (21) | 121.3 (6) |
| N (2) | C (7) | C (8) | 120.1 (5) | N (6) | C (21) | C (20) | 123.8 (6) |
| N (2) | C (7) | C (12) | 118.7 (5) | N (6) | C (22) | C (23) | 120.0 (5) |
| N (6) | C (22) | C (27) | 119.0 (5) | C (23) | C (22) | C (27) | 120.9 (5) |
| N (5) | C (23) | C (22) | 120.1 (5) | N (5) | C (23) | C (24) | 119.9 (5) |
| C (22) | C (23) | C (24) | 119.9 (6) | C (23) | C (24) | C (25) | 119.3 (6) |
| N (7) | C (25) | C (24) | 130.6 (5) | N (7) | C (25) | C (26) | 109.7 (5) |
| C (24) | C (25) | C (26) | 119.7 (5) | N (8) | C (26) | C (25) | 104.8 (5) |
| N (8) | C (26) | C (25) | 104.8 (5) | N (8) | C (26) | C (27) | 132.1 (5) |
| C (25) | C (26) | C (27) | 123.1 (6) | C (22) | C (27) | C (26) | 117.1 (5) |
| N (7) | C (28) | N (8) | 113.4 (6) | N (7) | C (28) | C (29) | 125.2 (6) |
| N (8) | C (28) | C (29) | 121.4 (6) | | | | |

Angles are in degrees. Estimated standard deviations in the least significant figure are given in parentheses.

TABLE 5

Intramolecular distances involving the nonhydrogen atoms AG2044

| atom | atom | distance | atom | atom | distance |
|---|---|---|---|---|---|
| S (1) | C (1) | 1.712 (3) | C (1) | C (5) | 1.457 (4) |
| S (1) | C (4) | 1.685 (4) | C (2) | C (3) | 1.440 (5) |
| S (2) | C (16) | 1.718 (3) | C (3) | C (4) | 1.346 (5) |
| S (2) | C (19) | 1.712 (3) | C (5) | C (6) | 1.417 (4) |
| N (1) | C (5) | 1.321 (4) | C (7) | C (8) | 1.430 (4) |
| N (1) | C (8) | 1.361 (4) | C (7) | C (12) | 1.394 (4) |
| N (2) | C (6) | 1.304 (4) | C (8) | C (9) | 1.407 (4) |
| N (2) | C (7) | 1.372 (4) | C (9) | C (10) | 1.368 (4) |
| N (3) | C (10) | 1.382 (4) | C (10) | C (11) | 1.418 (4) |
| N (3) | C (13) | 1.367 (4) | C (11) | C (12) | 1.379 (5) |
| N (3) | C (14) | 1.447 (4) | C (13) | C (15) | 1.496 (5) |
| N (4) | C (11) | 1.386 (4) | C (16) | C (17) | 1.370 (4) |
| N (4) | C (13) | 1.301 (5) | C (16) | C (20) | 1.455 (4) |
| N (5) | C (20) | 1.319 (4) | C (17) | C (18) | 1.417 (5) |
| N (5) | C (23) | 1.370 (4) | C (18) | C (19) | 1.332 (5) |
| N (6) | C (21) | 1.294 (4) | C (20) | C (21) | 1.428 (4) |
| N (6) | C (22) | 1.374 (4) | C (22) | C (23) | 1.439 (4) |
| N (7) | C (25) | 1.380 (4) | C (22) | C (27) | 1.386 (4) |
| N (7) | C (29) | 1.447 (4) | C (24) | C (25) | 1.370 (4) |
| N (8) | C (26) | 1.388 (4) | C (25) | C (26) | 1.418 (4) |
| N (8) | C (28) | 1.312 (4) | C (26) | C (27) | 1.370 (4) |
| C (1) | C (2) | 1.396 (4) | C (28) | C (30) | 1.478 (4) |

Distances are in angstroms. Estimated standard deviations in the least significant figure are given in parentheses.

TABLE 6

Intramolecular bond angles involving the nonhydrogen atoms AG2044

| atom | atom | atom | angle | atom | atom | atom | angle |
|---|---|---|---|---|---|---|---|
| C (1) | S (1) | C (4) | 92.3 (2) | C (8) | C (7) | C (12) | 120.9 (3) |
| C (16) | S (2) | C (19) | 91.5 (2) | N (1) | C (8) | C (7) | 121.2 (3) |
| C (5) | N (1) | C (8) | 117.4 (2) | N (1) | C (8) | C (9) | 118.5 (3) |
| C (6) | N (2) | C (7) | 117.1 (3) | C (7) | C (8) | C (9) | 120.3 (3) |
| C (10) | N (3) | C (13) | 106.3 (3) | C (8) | C (9) | C (10) | 117.3 (3) |
| C (10) | N (3) | C (14) | 125.3 (3) | N (3) | C (10) | C (9) | 131.8 (3) |
| C (13) | N (3) | C (14) | 128.2 (3) | N (3) | C (10) | C (11) | 105.4 (3) |
| C (11) | N (4) | C (13) | 105.7 (3) | C (9) | C (10) | C (11) | 122.8 (3) |
| C (20) | N (5) | C (23) | 117.2 (3) | N (4) | C (11) | C (10) | 108.9 (3) |
| C (21) | N (6) | C (22) | 117.2 (3) | N (4) | C (11) | C (12) | 130.7 (3) |
| C (25) | N (7) | C (28) | 106.9 (2) | C (10) | C (11) | C (12) | 120.4 (3) |
| C (25) | N (7) | C (29) | 125.1 (2) | C (7) | C (12) | C (11) | 118.2 (3) |
| C (28) | N (7) | C (29) | 128.0 (3) | N (3) | C (13) | N (4) | 113.6 (3) |
| C (26) | N (8) | C (28) | 105.5 (3) | N (3) | C (13) | C (15) | 122.0 (4) |
| S (1) | C (1) | C (2) | 112.2 (2) | N (4) | C (13) | C (15) | 124.4 (4) |
| S (1) | C (1) | C (5) | 119.5 (2) | S (2) | C (16) | C (17) | 110.9 (2) |
| C (2) | C (1) | C (5) | 128.3 (3) | S (2) | C (16) | C (20) | 119.8 (2) |
| C (1) | C (2) | C (3) | 109.1 (3) | C (17) | C (16) | C (20) | 129.3 (3) |
| C (2) | C (3) | C (4) | 114.1 (3) | C (16) | C (17) | C (18) | 112.3 (3) |
| S (1) | C (4) | C (3) | 112.3 (3) | C (17) | C (18) | C (19) | 113.0 (3) |
| N (1) | C (5) | C (1) | 117.7 (3) | C (18) | C (19) | S (2) | 112.3 (3) |
| N (1) | C (5) | C (6) | 120.9 (3) | N (5) | C (20) | C (16) | 117.9 (3) |
| C (1) | C (5) | C (6) | 121.3 (3) | N (5) | C (20) | C (21) | 121.2 (3) |
| N (2) | C (6) | C (5) | 123.6 (3) | C (16) | C (20) | C (21) | 120.9 (3) |
| N (2) | C (7) | C (8) | 119.8 (3) | N (6) | C (21) | C (20) | 123.5 (3) |
| N (2) | C (7) | C (12) | 119.3 (3) | N (6) | C (22) | C (23) | 119.9 (3) |
| N (6) | C (22) | C (27) | 119.7 (3) | C (23) | C (22) | C (27) | 120.4 (3) |
| N (5) | C (23) | C (22) | 120.8 (3) | N (5) | C (23) | C (24) | 118.6 (3) |
| C (22) | C (23) | C (24) | 120.5 (3) | C (23) | C (24) | C (25) | 117.2 (3) |
| N (7) | C (25) | C (24) | 132.0 (3) | N (7) | C (25) | C (26) | 105.2 (2) |
| C (24) | C (25) | C (26) | 122.9 (3) | N (8) | C (26) | C (25) | 109.4 (2) |
| N (8) | C (26) | C (27) | 130.6 (3) | C (25) | C (26) | C (27) | 120.1 (3) |
| C (22) | C (27) | C (26) | 118.9 (3) | N (7) | C (28) | N (8) | 113.1 (3) |
| N (7) | C (28) | C (30) | 121.9 (3) | N (8) | C (28) | C (30) | 125.0 (3) |

Angles are in degrees. Estimated standard deviations in the least significant figure are given in parentheses.

TABLE 7

Intermolecular distances involving the nonhydrogen atoms AG2044

| atom | atom | distance | ADC (*) |
|---|---|---|---|
| O (1w) | O (2w) | 2.764 (5) | 66703 |
| O (1w) | O (3w) | 2.777 (5) | 1 |
| O (1w) | N (4) | 2.825 (4) | 1 |
| O (2w) | O (3w) | 2.702 (5) | 1 |
| O (2w) | N (8) | 2.816 (4) | 1 |

Contacts out to 3.00 angstroms. Estimated standard deviations in the least significant figure are given in parentheses.

Example 2

Biological Analysis

Inhibition of PDGF-induced tyrosine phosphorylation by tyrphostins in vitro: A preparation of purified PDGFR from Swiss 3T3 cell membranes was used to assess and compare the inhibitory effects of tyrphostin compounds on tyrosine kinase activity. Various concentrations of the purified "transoid" isomers AG2033 and AG2043, were evaluated. Table 8 below presents $IC_{50}$ values (50% inhibition of phosphorylation, $\mu$M) of AG2033 and AG2043. Data presents the potencies of the compounds with respect to PDGFR, as was determined using the isolated receptor (see experimental methods section above).

TABLE 8

| Concentration ($\mu$M) | % of Control AG2033 | % of Control AG2043 |
| --- | --- | --- |
| 0 | 100 | 100 |
| 0.03 | 97.9 | 60.1 |
| 0.1 | 37 | 41.6 |
| 0.3 | 17.9 | 40.4 |
| 1 | 13.7 | 15.1 |
| 3 | 9.8 | 11 |
| IC$_{50}$ | 0.07 | 0.09 |

Figure 5:
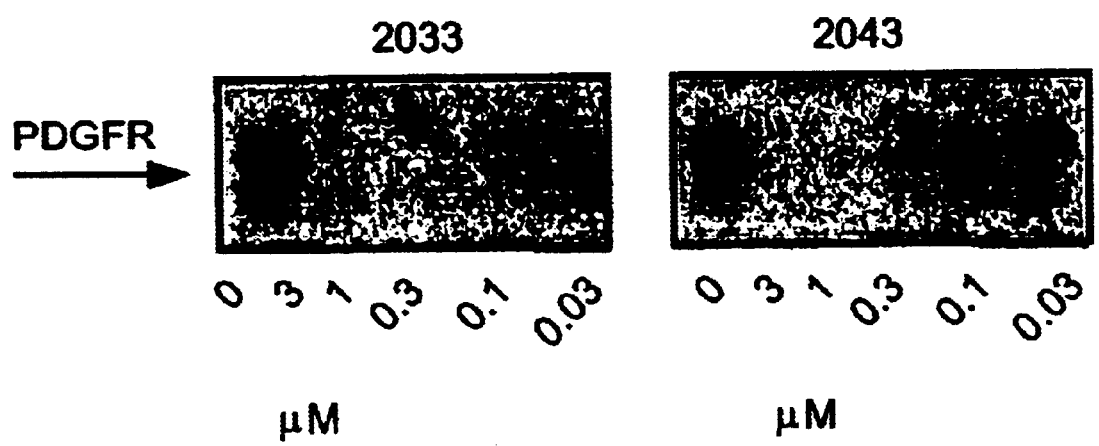
FIG. 5 presents radiograms demonstrating inhibition of PDGFR autophosphorylation in a cell free system derived from Swiss 3T3 cell membranes by AG2033 (1,2-dimethyl-6-phenyl imidazolo[5,4-g] quinoxaline) and AG2043 (1,2-dimethyl-6-(2-thiophene)imidazolo[5,4-g] quinoxaline) purified isomers.
Figure 6:
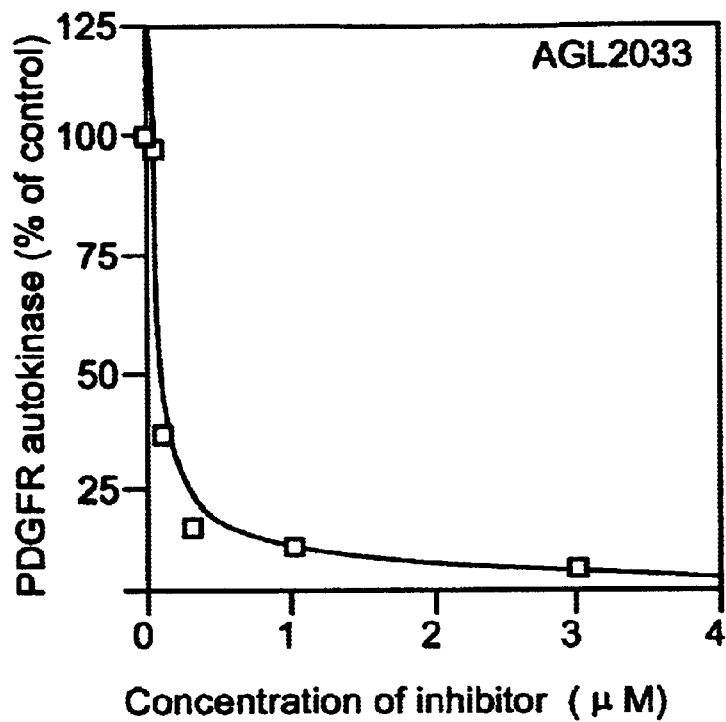
FIG. 6 shows a dose-response curve for purified AG2033 (1,2-dimethyl-6-phenyl imidazolo[5,4-g] quinoxaline) inhibitory effect on PDGFR autophosphorylation.
Figure 7:
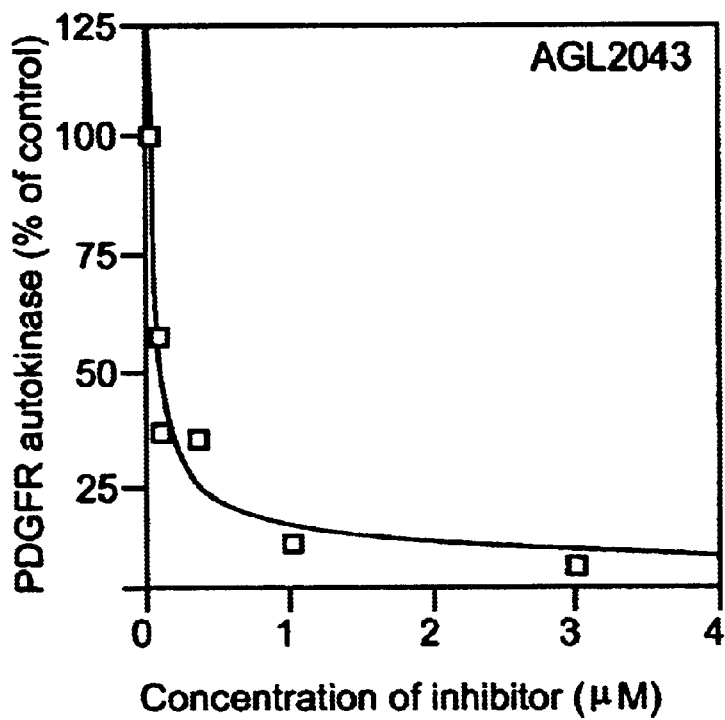
FIG. 7 shows a dose-response curve for purified AG2043 (1,2-dimethyl-6-(2-thiophene)imidazolo[5,4-g] quinoxaline) inhibitory effect on PDGFR autophosphorylation.
Figure 8:
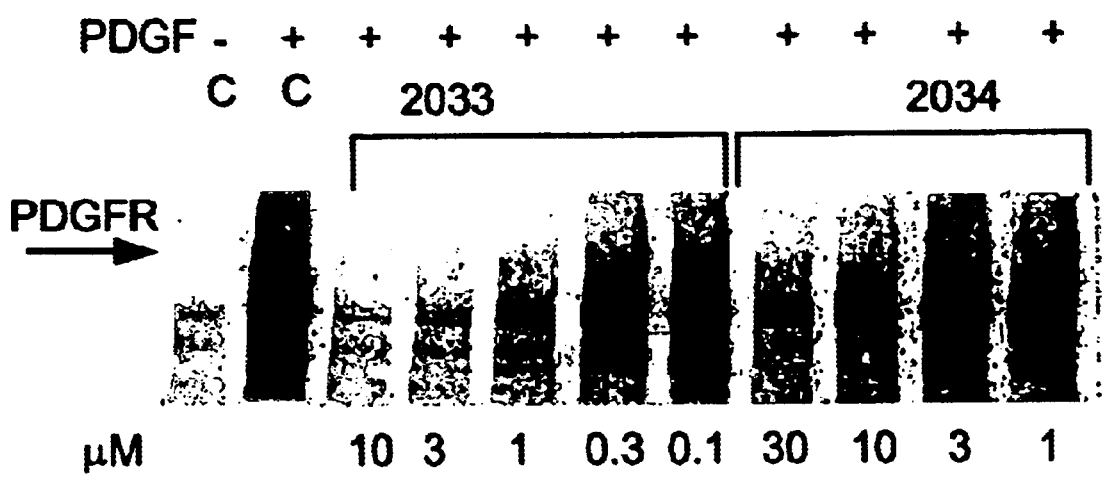
FIG. 8 presents radiograms demonstrating inhibition of PDGFR autophosphorylation in intact Swiss 3T3 cells comparing each isomer pair, AG2033 and AG2034 (1,2-dimethyl-6-phenyl imidazolo[5,4-g] quinoxaline, (1,2-dimethyl-7-phenyl imidazolo[5,4-g] quinoxaline, respectively); AG2043 and AG2044 (1,2-dimethyl-6-(2-thiophene)imidazolo[5,4-g] quinoxaline, (1,2-dimethyl-7-(2-thiophene)imidazolo[5,4-g] quinoxaline, respectively)
Figure 8:
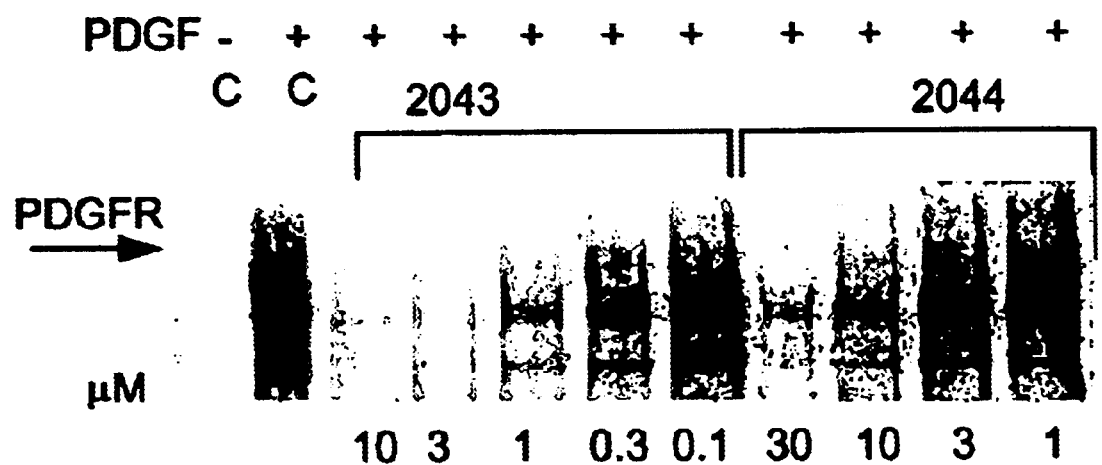

Kinase reactions, using an isolated PDGFβR preparation, in the presence of 0.03–3 $\mu$M tyrphostin, were conducted, utilizing [γ-$^{32}$P]ATP as probe. Analysis was conducted by subjecting samples to SDS-PAGE, radiograms thereof are presented in FIG. 5. Densitometric evaluation, relative to control lacking the tyrphostin inhibitor (100%), results in the percent autokinase activity, presented in Table 8 and in the dose-response curves for the purified transoid isomers AG2033 (FIG. 6) and AG2043 (FIG. 7). Further comparison between the resulting autoradiogrms for each pair of geometrical isomers AG2033 and AG2034 (upper panel); AG2043 and AG2044 (lower panel), for their inhibitory activity towards PDGF-induced PDGFβR autophosphorylation (concentration range: 0.1–10 $\mu$M) in intact cells is presented in FIG. 8. While marked inhibitory activity is present for the "transoid" isomer AG2033 at 1 $\mu$M, similar inhibition exists only at much higher concentrations (10–30 $\mu$M) of the "cisoid" isomer AG2034. This data proves AG2033 as having superior activity (higher potency) compared to the AG2034 isomer. Similar potency relation exists between the AG2043 and AG2044 isomers.

Inhibition of PDGF-Induced Tyrosine Phosphorylation of Intact Cells by Tyrphostins:

Stimulation of porcine aortic endothelial cells (PAEC) with PDGF-BB (100 ng/ml) resulted in strong phosphorylation of the PDGF β-receptor on tyrosine residues. Addition of tyrphostin compounds to the cells prior to PDGF-stimulation completely inhibited PDGF β-receptor tyrosine-phosphorylation. Table 9 below presents IC$_{50}$ values (50% inhibition of phosphorylation, $\mu$M) of various tyrphostins, AG1295 (which serves as a positive control), and the purified isomers of AG1851: AG2033, AG2034 and AG1992: AG2043, AG2044. The data in Table 9 presents the differential potencies of the various compounds with respect to PDGFR and KDR, as was performed on intact PAEC cells expressing these receptors (see experimental methods section above).

TABLE 9

| Compound | PDGFR | KDR |
| --- | --- | --- |
| AG2033 | 0.5 | >10 |
| AG2034 | 10.0 | n.d. |
| AG2043 | 1.0 | 3.0 |
| AG2044 | 5.0 | n.d. |
| AG1295 | n.d. | 1.0 | n.d = not determined

These compounds do not inhibit other tyrosine kinase receptors at concentrations below 75 $\mu$M. The only receptor affected by the above mentioned compounds is the KDR/VEGFR, but only at concentrations that are at least 3–20-fold higher as compared to those effecting PDGFR kinase. Thus, these compounds constitute effective and selective PDGFR kinase blockers. Furthermore, for each isomers' pair (AG2033, AG2034 and AG2043, AG2044) higher potencies are evident for the "transoid" isomer (AG2033, AG2043) relative to the "cisoid" isomer (AG2034, AG2044).

Effects of Tyrphostins on Cell Proliferation:

Pig heart smooth muscle cells (SMC): Treatment of pig heart smooth muscle cells (SMC) with AG1992-derived purified isomers, AG2043 and AG2044, as well as AG1295 (10 $\mu$M each) resulted in 46%, 84% and 61%, respectively, mean reduction in SMC count by day 3 as is compared to DMSO treated control cells. As further described below, the inhibitory effect of AG2043, AG2044 and AG1295 was completely reversible.

Figure 9:
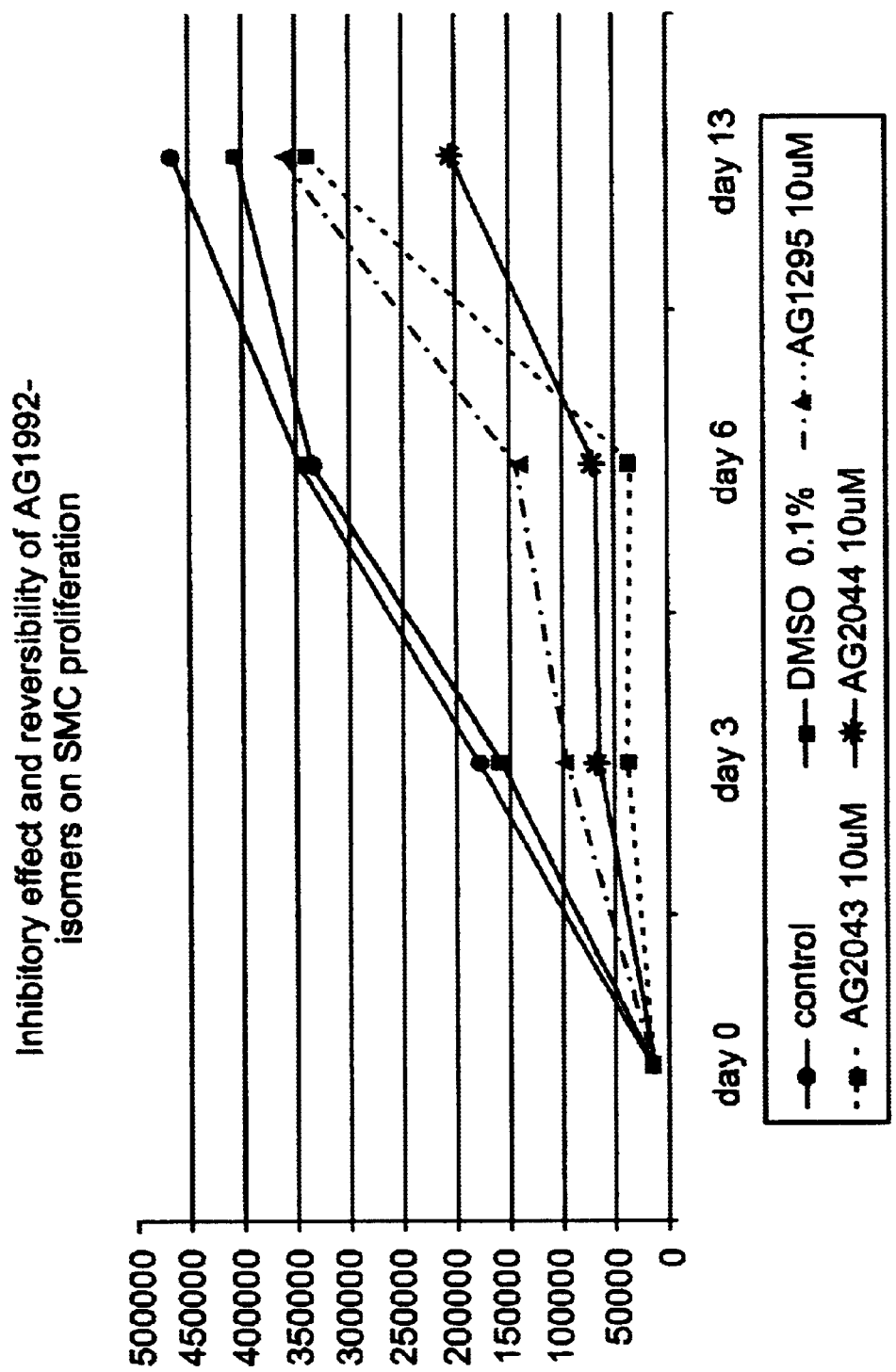
FIG. 9 presents plots demonstrating the inhibitory and recovery effects of purified AG2043 and AG2044 isomers (1,2-dimethyl-6-(2-thiophene)imidazolo[5,4-g] quinoxaline, (1,2-dimethyl-7-(2-thiophene)imidazolo[5,4-g] quinoxaline, respectively) on porcine SMC proliferation.

FIG. 9 demonstrates the inhibitory and recovery effects of AG1992-derived purified isomers, AG2043 and AG2044, as well as AG1295 on pig heart SMC proliferation. Cells were grown in the presence of the specified tyrphostins and were counted on days 3, 6 and 13 in culture. On day 7 the cultures were washed and the cells allowed to recover. All three tyrphostins showed potent growth inhibition effect as compared with controls. The "transoid" isomer, AG2043, exhibited higher inhibitory potency as compared its counterpart "cisoid" isomer, AG2044. At the 10 $\mu$M concentration, AG2043 induced the most effective inhibition, without having a substantial toxic effect on the cells. The inhibitory effect of all three compounds was reversible, and the cells resumed normal growth response as soon as the treatment with the tyrphostins was withdrawn.

Porcine Aortic Endothelial Cells (PAEC):

Inhibitory effects of tyrphostin compounds on PDGF-induced proliferation were further evaluated on PAEC cells.

Table 10 below presents the IC$_{50}$ values (50% inhibition of proliferation, $\mu$M) of purified AG2033 isomer, on PDGFR and KDR of transfected PAEC cells.

TABLE 10

| Compound | PDGFβR | KDR |
| --- | --- | --- |
| AG2033 | 2.5 | >10 |

Similar to the inhibition results obtained on the respective receptors' autophosphorylation, the purified tyrphostin AG2033 demonstrated potent and selective inhibition of PDGFβR transfected PAEC cell proliferation. Similar results were obtained with human coronary artery endothelial cells (HCAEC).

Effects of Tyrphostins on Cell Migration:

Evaluation of PDGFβR or KDR stably transfected PAEC cells migration toward the respective growth factors, PDGD-BB and VEGF (10 ng/ml, respectively), in the presence of the purified AG2033 isomer, was conducted in a Boyden chamber (see experimental section, above). Table 11 below presents IC$_{50}$ values (50% inhibition of migration, $\mu$M) for the AG2033 isomer with respect to PDGFR and KDR, as was performed on PAEC cells.

TABLE 11

| Compound | PDGFβR | KDR |
| --- | --- | --- |
| AG2033 | 5.0 | >10 |

In high accordance with the inhibition of autophosphorylation results described above with respect to PAEC cells, as well as with the proliferation results, the purified tyrphostin AG2033 demonstrates potent and selective inhibition of PAEC cell migration.

Further evaluation of HCASMC cells migration toward PDGD-BB, in the presence of purified "transoid" isomers, was conducted in a Boyden chamber (see experimental section, above).

Figure 10:
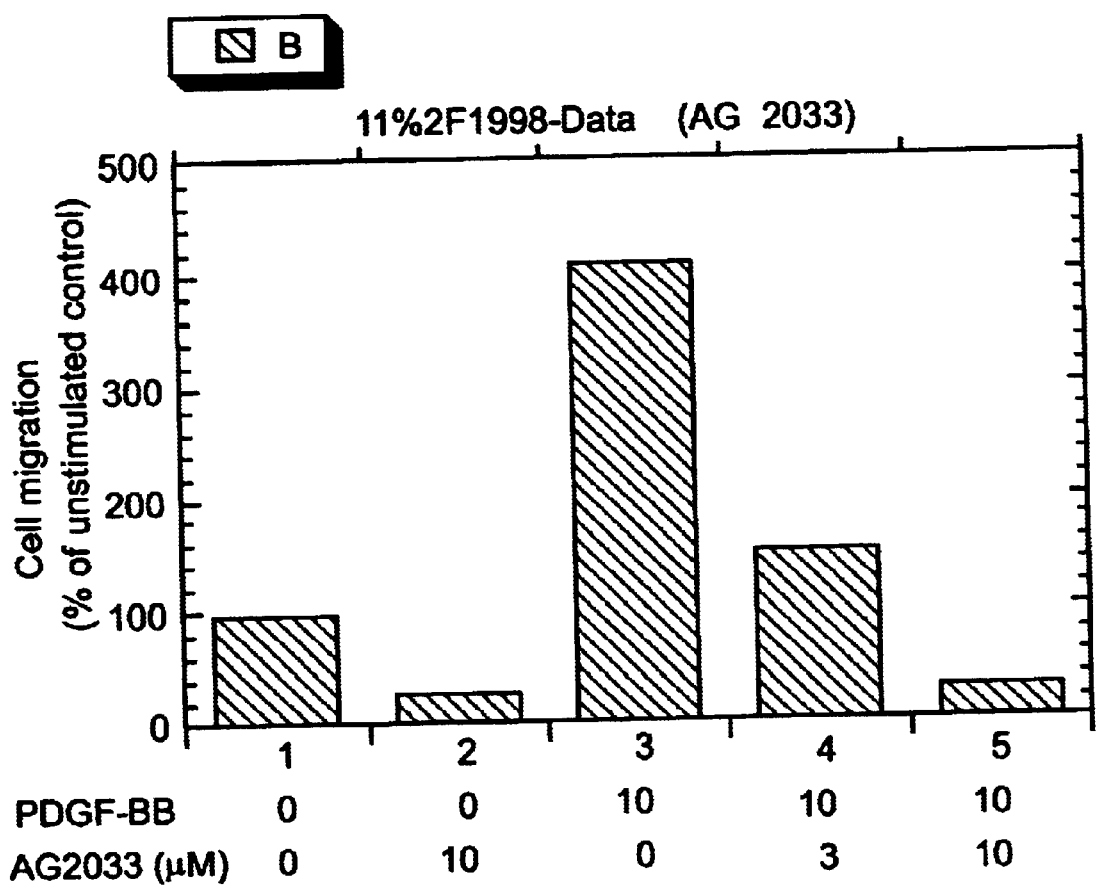
FIG. 10 is a bar graph, demonstrating the inhibitory effect of purified AG2033 isomer (1,2-dimethyl-6-phenyl imidazolo[5,4-g] quinoxaline) on human coronary artery SMC (HCASMC) migration.

FIG. 10 presents data obtained with AG2033. Potent inhibition of the purified tyrphostin isomer is evident in both the absence and presence of PDGF-BB growth factor, i.e., dose-dependent inhibition is achieved of both the basal ($IC_{50}<10$ $\mu$M) and the induced ($IC_5<3$ $\mu$M) migratory activity of the HCASMC cells. These results correlate with the hereinabove described inhibitory effects of AG2033 on PAEC cell migration, and effects obtained on receptor autophosphorylation.

Figure 11:
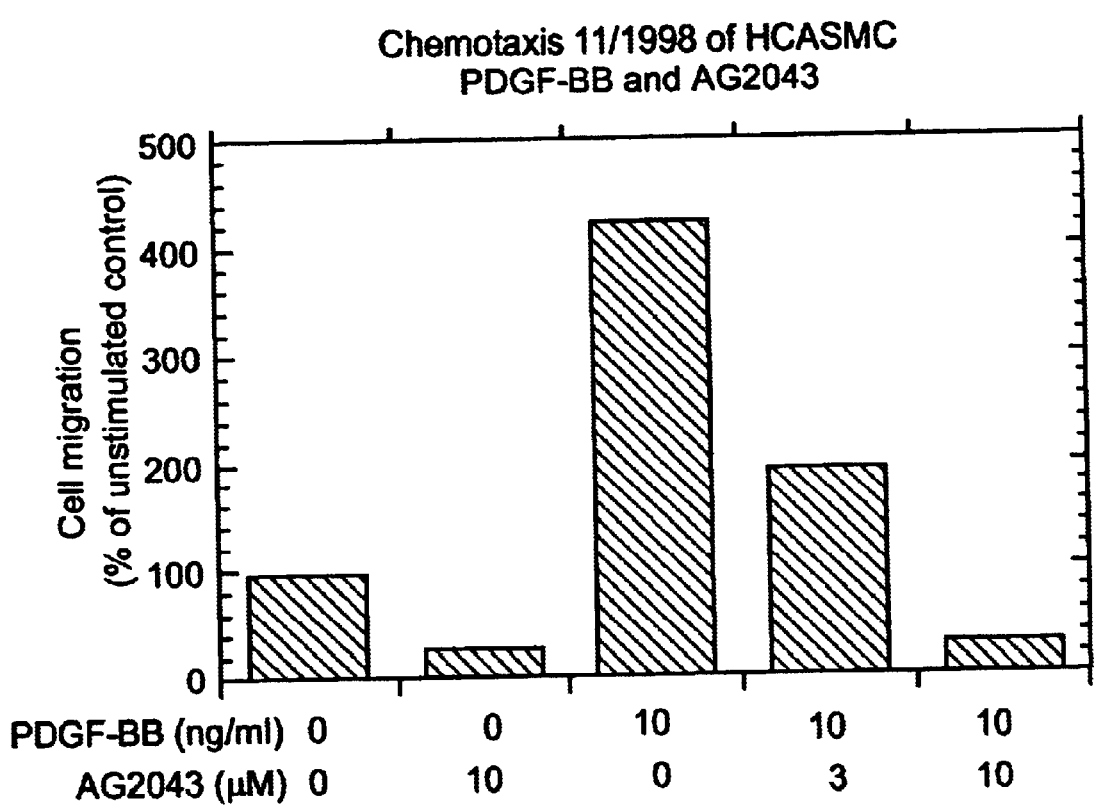
FIG. 11 is a bar graph, demonstrating the inhibitory effect of purified AG2043 isomer (1,2-dimethyl-6-(2-thiophene) imidazolo[5,4-g] quinoxaline) on human coronary artery SMC (HCASMC) migration.

Similarly, FIG. 11 presents data obtained with AG2043. Again, potent inhibition of the purified tyrphostin isomer is evident in both the absence and presence of PDGF-BB growth factor, i.e., dose-dependent inhibition is achieved of both the basal ($IC_{50}<10$ $\mu$M) and the induced ($IC_{50}\sim3$ $\mu$M) migratory activity of the HCASMC cells. These results correlate with the above described inhibitory effects of AG2043 on receptor autophosphorylation and porcine SMC proliferation.

A Pharmaceutical Composition of and Method for In Vitro Tyrphostins Delivery:

According to the present invention tyrphostins are delivered to a balloon treated area of an artery by coating the balloon with tyrphostin slow release nanoparticles which slowly discharge the tyrphostin at the balloon treated area, thereby cell proliferation at the treated area is inhibited.

To this end a tyrphostin compound is formulated in nanoparticles, for example, polylactic acid (PLA) nanoparticles loaded with tyrphostin prepared by an oil-in-water (O/W) emulsification/solvent evaporation method as follows.

Fifty mg PLA and 3 mg of the selected tyrphostin(s) are dissolved in an organic mixture of 0.5 ml dichloromethane and 10 ml acetone. The organic solution is added to 20 ml of an aqueous solution containing 0.5% Poloxamer F68. The oil-in-water (O/W)-type emulsion is stirred by means of a magnetic stirrer at 20 W power output for 5 minute. The organic solvents are evaporated in a rotating evaporator at pressure of 20 mm Hg, giving a colloidal suspension of nanoparticles. Finally, the obtained suspension is passed through a Whatman 40 filter paper.

This formulation may be employed for inhibiting cell proliferation via slow release mechanism in various proliferative disorders, including, but not limited to, psoriasis, papilloma, restenosis, atherosclerosis, in-stent stenosis, vascular graft restenosis, pulmonary fibrosis, glomerular nephritis, rheumatoid arthritis and PDGF receptor associated malignancies.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES CITED

1. Ross. R. Platelet-derived growth factor. Lancet, 1:1179–1182, 1989.
2. Heldin, C. H. Structural and functional studies on platelet-derived growth factor. EMBO J., 11: 4251–4259,1992.
3. Yarden, Y., Escobedo, J. A., Kuang, W-J., Yang-Feng, T. L., Daniel, T. O. Tremble, P. M., Chen, E. Y., Ando, M. E., Harkins, R. N., Franeke, U., Friend, V. A., Ullrich, A., Williams, L. T. Structure of the receptor for platelet-derived growth factor helps define a family of closely related growth factor receptors. Nature (Lond.), 323: 226–232,1986.
4. Matsui, T., Heidaran, M., Miki, T., Popescu, N., LaRochelle, W., Kraus, M., Pierce, J., and Aatonson, S. Isolation of a novel receptor cDNA establishes the existence of two PDGF receptor genes. Science (Washington D.C.), 243: 800–804, 1989.
5. Claesson-Welsh, L., Eriksson, A., Westermark, B., and Heldin, C-H. cDNA cloning and expression of the human A-type platelet-derived growth factor (PDGF) receptor establishes structural similarity to the B-type PDGF receptor. Proc. Natl. Acad. Sci. USA, 86: 4917–4921, 1989.
6. Escobedo, J. A., Barr, P. J., and Williams, L. T. Role of tyrosine kinase and membrane-spanning domains in signal transduction by platelet-derived growth factor receptor. Mol. Cell. Biol., 8: 5126–5131, 1988.
7. Ross, R. Mechanisms of atherosclerosis-a review. Adv. Nephrol. Necker Hosp., 19: 79–86, 1990.
8. Ross, R. The pathogenesis of atherosclerosis: a perspective for the 1990s. Nature (Lond.) 362: 801–809, 1993.
9. Shaw, R. J., Benedict, 5. H., Clark, . A., and King, T. E. Pathogenesis of pulmonary fibrosis in interstitial lung disease. Alveolar macrophage PDGF(B) gene activation and up-regulation by interferon -γ. Am. Rev. Respir. Dis., 143: 167–173, 1991.
10. Gesualdo, L., Ranierei, E., Pannarale, G., Di Paoio, S., and Schena, F. P. Platelet-derived growth factor and proliferative glomerulonephritis. Kidney Int., 43 (Suppl. 39): 86 89, 1993.
11. Rubin, K., Terracio, L., Ronnstrand, L., Heldin, C. H., and Klareskog, L. Expression of platelet-derived growth factor receptors is induced on connective tissue cells during chronic synovial inflammation. Scand. J. Immunol., 27:285–294, 1988.
12. Waterfield, M. D., Scrace, G. T., Whittle, N., Stroobant, P., Johnson, A., Wasteson, A., Westermark, B., Heldin, C. H., Huang, J. S., and Deuel, T, F. Platelet-derived growth factor is structurally related to the putative transforming protein p28 sis of simian sarcoma virus. Nature (Lond.), 304: 35–39, 1983.
13. Doolittle, R. F., Hunkapiller, M. W., Hood, L. E., Devare, S. G., Robbins, K. C., Aaronson, S. A., and Antoniades, H. N. Simian sarcoma virus oncogene, v-sis, is derived from the gene (or genes) encoding a platelet-derived growth factor. Science (Washington D.C.), 221: 275–277, 1983.
14. Heldin, C-H., and Westermark, B. Platelet-derived growth factor and autocrine mechanisms of oncogenic processes. CRC Crit. Rev. Oncog., 2:109–124, 1991.
15. Engstrom, U., Engstrom, A., Ernlund, A., Westermark, B., and Heldin, C-H. Identification of a peptide antagonist for platelet-derived growth factor. J. Biol. Chem., 267: 16581–16587,1992.
16. Vassbotn, F. S., Andersson, M., Westermark, B., Heldin, C. H., and Ostman, A. Reversion of autocrine transformation by a dominant negative platelet-derived growth factor mutant. Mol. Cell. Biol., 13: 4066–4076, 1993.
17. Shamah, S. M., Stiles, C. D., and Guha, A. Dominant-negative mutants of platelet-derived growth factor revert the transformed phenotype of human astrocytoma cells. Mol. Cell. Biol., 13: 7203–7212, 1993.

18. Ueno, H. Colbert, H., Escobedo, J. A., and Williams, L. T. Inhibition of PDGFR receptor signal transduction by coexpression of a truncated receptor. Science (Washington D.C.), 252: 844–848, 1991.
19. Levitzki, A. Tyrphostins: tyrosine kinase blockers as novel antiproliferative agents and dissectors of signal transduction. FASEB J., 6: 3275–3282, 1992.
20. Bilder, G. E., Krawiec, J. A., McVety, K., Gazit, A., Gilon, C., Lyall, R., Zilberstein A., Levitzki, A., Perrone, M. H., and Schreiber, A. B. Tyrphostins inhibit PDGF induced DNA synthesis acid associated early events in smooth mucells. Am. J. Physiol., 260: C721-C730, 1991.
21. Bryckaert, M. C., Eldor, A., Fontanay, M., Gazit, A., Osherov, N., Gilon, C., Levitzki, A., and Tobelem, G. Inhibition of platelet-derived growth factor-induced mitogenesis and tyrosine kinase activity in cultured bone marrow fibroblasts by tyrphostins. Exp. Cell. Res., 199: 255–261, 1992.
22. Kovalenko, M., Gazit, A., Bohmer, A., Rorsman, C., Ronnstrand, L., Heldin, C. H., Waltenberger J., Bohmer F. D., and Levitzki A. Selective platelet-derived growth factor receptor kinase blockers reverse sis-transformation. Cancer Research, 54:6106–6 114.
23. Kovalenko, M., Ronnstrand, L., Heldin, C. H., Loubtchekov, M., Gazit, A., Levitzki, A., and Bohmer F. D. Phosphorylation site-specific inhibition of platelet-derived growth factor β-receptor autophosphorylation by the receptor blocking tryphostin AG 1296. Biochemistry, 36:6260–6269.
24. Golomb, G., Fishbein, I., Banai, S., Mishaly, D., Moscovitz. D., S. Gertz, D., Gazit, A., Levitzki, A. Controlled delivery of a tyrphostin inhibits intimal hyperplasia in a rat carotid artery injury model. Artherosclerosis, 125:171–182, 1996.
25. Sirois, M. G., Simms, M., Edelman, E. R. Antisense oligonucleotide inhibition of PDGF-β subunit expression directs suppression of intimal thickening. Circulation, 95:669–676, 1977.
26. Eriksson, A., Siegbahn, A., Westerinark, B., Heldin, C. H., and Claesson-Welsh, L. PDGF α- and β-receptors activate unique and common signal transduction pathways. EMBO J., 11: 543–5 50, 1992.
27. Waltenberger, J., Claesson-Welsh, L., Siegbahn, A., Shibuya, M., and Heldin C. H. J. Blot. Chem. 269: 26988–26995, 1994.
28. Oberg, C., Waltenberger, J., Claesson-Welsh, L., Welsh, M. Expression of protein tyrosirie kinases in isley cells: possible role of the flk-1 receptor for β-cell maturation from duct cells. Growth Factors 10:115–126, 1994.
29. Westermark, B., Siegbahn, A., Heldin, C. H. and Claesson-Welsh, L. Proc. Natl. Acad. Sd. USA 87: 128–132, 1990.
30. Sheldrick, G. M. Crystallographoc computing 3, Oxford University Press, pp. 175–189, 1985.
31. Akbasak and Suner, J. Neurol Sd, 111:119–133, 1992.
32. Dickson et al., Cancer Treatment Res. 61:249–273, 1992.
33. Korc et al., J. Clin. Invest. 90:1352–1360, 1992.
34. Krohnke, C. Chem. Ber. 69: 2006, 1936.

What is claimed is:
1. A purified tyrphostin of a general formula:

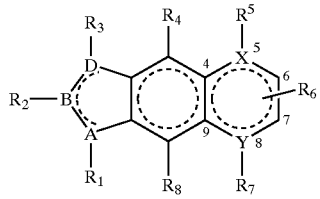

(Compound I)

wherein,
4, 5, 6, 7, 8 and 9 indicate positions on a terminal 6-member ring;
A, D, X and Y are each a nitrogen;
B is a carbon;
$R_1, R_2, R_3, R_5$ and $R_7$ are each independently selected from the group consisting of hydrogen, alkyl, alkenyl, alkynyl, cycloalkyl, aryl, hydroxy, alkoxy, halo, C-carboxy, O-carboxy, carbonyl, thiocarbonyl, C-amido, guanly, sulfonyl, trihalomethane-sulfonyl and a pair of electrons, or alternatively, $R_1$ and $R_2$ or $R_2$ and $R_3$ form a 5-7 member ring structure;
$R_6$ is selected from the group consisting of alkyl, trihaloalkyl, cycloalkyl, alkenyl, alkynyl, aryl, heteroaryl, heteroalicyclic, hydroxy, alkoxy, a ryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and a physiologically acceptable salt or a prodrug thereof;
$R_4$ and $R_8$ are each independently selected from the group consisting of hydrogen, alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and $—NR_{10}R_{11}$ and, a physiologically acceptable salt or a prodrug thereof;
$R_{10}$ and $R_{11}$ are each independently selected from the group consisting of hydrogen, alkyl, cycloalkyl, aryl, carbonyl and sulfonyl, or alternatively $R_{10}$ and $R_{11}$ form a five- or six-member heteroalicyclic ring; and, a physiologically acceptable salt or a prodrug thereof;
whereas, for Compound I, said $R_6$ is either at position 6 or at position 7.
2. The purified tyrphostin of claim 1, wherein
$R_1$ and $R_2$ are each independently selected from the group consisting of alkyl, alkoxy, halogen, nitro and amine group;
$R_3$, $R_5$ and $R_7$ are each a pair of electrons;
$R_6$ is an aryl, selected from the group consisting of phenyl, ferrocene, thiophene, furane, pyrrole, indole, thiazole, imidazole and pyridine.
3. The purified tyrphostin of claim 2, wherein
$R_1$ and $R_2$ are each a methyl;
$R_4$ and $R_8$ are each a hydrogen.
4. The purified tyrphostin of claim 1, wherein for Compound I said $R_6$ is at position 6.

5. The purified tyrphostin of claim 1, wherein Compound I said $R_6$ is at position 7.

6. A pharmaceutical composition comprising, as an active ingredient, the purified tyrphostin of claim 1 and a pharmaceutically acceptable carrier.

7. The pharmaceutical composition of claim 6, wherein said pharmaceutically acceptable carrier is a slow release carrier.

8. The pharmaceutical composition of claim 7, wherein said slow release carrier is polylactic acid.

9. A method of treating or preventing a protein tyrosine kinase related disorder in an organism, the method comprising the step of administering to said organism a therapeutically effective amount of the pharmaceutical composition of claim 7.

10. The method of claim 9, wherein said protein tyrosine kinase related disorder is selected from the group consisting of an EGF related disorder, a PDGF related disorder, an IGF related disorder and a met related disorder.

11. The method of claim 9, wherein said protein tyrosine kinase related disorder is selected from the group consisting of a cell proliferative disorder, a fibrotic disorder and a metabolic disorder.

12. The method of claim 11, wherein said cell proliferative disorder is selected from the group consisting of papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's disease, Burkitt's disease, arthritis, rheumatoid arthritis, diabetic retinopathy, angiogenesis, restenosis, in-stent restenosis, vascular graft restenosis.

13. The method of claim 11, wherein said cell fibrotic disorder is selected from the group consisting of pulmonary fibrosis, hepatic cirrhosis, atherosclerosis, glomerulonephritis, diabetic nephropathy, thrombic microangiopathy syndromes, transplant rejection.

14. The method of claim 11, wherein said cell metabolic disorder is selected from the group consisting of psoriasis, diabetes, wound healing, inflammation, and neurodegenerative diseases.

15. The method of claim 9, wherein said protein tyrosine kinase related disorder is selected from the group consisting of papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, small-cell lung cancer, colorectal cancer, thyroid cancer, pancreatic cancer, gastric cancer, hepatocellular carcinoma, leukemia, lymphoma, Hodgkin's disease, Burkitt's disease, psoriasis, pulmonary fibrosis, arthritis, rheumatoid arthritis, diabetic retinopathy, restenosis, in-stent restenosis, vascular graft restenosis, hepatic cirrhosis, atherosclerosis, angiogenesis, glomerulonephritis, diabetic nephropathy, thrombic microangiopathy syndromes, transplant rejection, autoimmune disease, wound healing, inflammation, neurodegenerative diseases, diabetes and hyperimmune disorders.

16. The method of claim 9, wherein said organism is a mammal.

17. The method of claim 16, wherein said mammal is a human.

18. A method of locally treating or preventing a disorder of a tissue of an organism comprising the step of locally applying the pharmaceutical composition of claim 6 onto said tissue.

19. The method of claim 18, wherein said organism is a human.

20. The method of claim 18, wherein said tissue is selected from the group consisting of blood vessel, lung and skin.

21. A method of inhibiting cell proliferation comprising the step of subjecting the cells to the purified tyrphostin of claim 1.

22. The method of claim 21, wherein said cells are of an organism, whereas subjecting the cells to said purified tyrphostin is effected in vivo.

23. The method of claim 22, wherein said organism is a human.

24. The method of claim 21, wherein subjecting the cells to said purified tyrphostin is effected in vitro.

25. A method of enriching, for a specific isomer, a tyrphostin of a general formula:

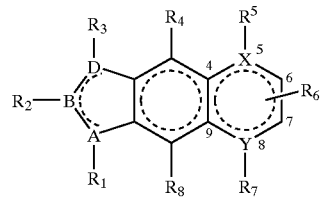

(Compound I)

wherein, 4, 5, 6, 7, 8 and 9 indicate positions on a terminal 6-member ring;

A, D, X and Y are each a nitrogen;

B is a carbon;

$R_1$, $R_2$, $R_3$, $R_5$ and $R_7$ are each independently selected from the group consisting of hydrogen, alkyl, alkenyl, alkynyl, cycloalkyl, aryl, hydroxy, alkoxy, halo, C-carboxy, O-carboxy, carbonyl, thiocarbonyl, C-amido, guanly, sulfonyl, trihalomethane-sulfonyl and a pair of electrons, or alternatively, $R_1$ and $R_2$ or $R_2$ and $R_3$ form a 5-7 member ring structure;

$R_6$ is selected from the group consisting of alkyl, trihaloalkyl, cycloalkyl, alkenyl, alkynyl, aryl, heteroaryl, heteroalicyclic, hydroxy, alkoxy, a ryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and a physiologically acceptable salt or a prodrug thereof;

$R_4$ and $R_8$ are each independently selected from the group consisting of hydrogen, alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and —$NR_{10}R_{11}$ and, a physiologically acceptable salt or a prodrug thereof;

$R_{10}$ and $R_{11}$ are each independently selected from the group consisting of hydrogen, alkyl, cycloalkyl, aryl, carbonyl and sulfonyl, or alternatively $R_{10}$ and $R_{11}$ form a five- or six-member heteroalicyclic ring; and, a physiologically acceptable salt or a prodrug thereof;

whereas, for each molecule of Compound I, $R_6$ is at position 6 or 7; the method comprising:
(a) chromatographing said tyrphostin through a matrix, thereby separating isomers of said tyrphostin; and
(b) collecting at least one specific isomer.

26. The method of claim 25, further comprising the step of:
(c) crystallizing said at least one specific isomer.

27. The method of claim 25, wherein
$R_1$ and $R_2$ are each independently selected from the group consisting of alkyl, alkoxy, halogen, nitro and amine group;
$R_3$, $R_5$ and $R_7$ are each a pair of electrons;
$R_6$ is an aryl, selected from the group consisting of phenyl, ferrocene, thiophene, furane, pyrrole, indole, thiazole, imidazole and pyridine.

28. The method of claim 27, wherein
$R_1$ and $R_2$ are each a methyl;
$R_4$ and $R_8$ are each a hydrogen.

29. A method for preparing a pharmaceutical composition for slow release of a tyrphostin comprising the steps of:
(a) providing a purified tyrphostin of a general formula:

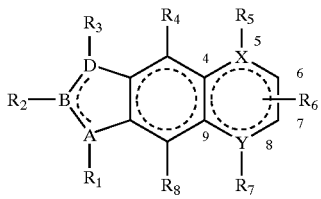

(Compound I)

wherein,
4, 5, 6, 7, 8 and 9 indicate positions on a terminal 6-member ring;
A, D, X and Y are each independently a nitrogen;
B is a carbon;
$R_1$, $R_2$, $R_3$, $R_5$ and $R_7$ are each independently selected from the group consisting of hydrogen, alkyl, alkenyl, alkynyl, cycloalkyl, aryl, hydroxy, alkoxy, halo, C-carboxy, O-carboxy, carbonyl, thiocarbonyl, C-amido, guanly, sulfonyl, trihalomethane-sulfonyl and a pair of electrons, or alternatively, $R_1$ and $R_2$ or $R_2$ and $R_3$ form a 5-7 member ring structure;
$R_6$ is selected from the group consisting of alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and a physiologically acceptable salt or a prodrug thereof;
$R_4$ and $R_8$ are each independently selected from the group consisting of hydrogen, alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and —$NR_{10}R_{11}$ and, a physiologically acceptable salt or a prodrug thereof;
$R_{10}$ and $R_{11}$ are each independently selected from the group consisting of hydrogen, alkyl, cycloalkyl, aryl, carbonyl and sulfonyl, or alternatively $R_{10}$ and $R_{11}$ form a five- or six-member heteroalicyclic ring; and, a physiologically acceptable salt or a prodrug thereof;
whereas, for Compound I, said $R_6$ is either at position 6 or at position 7;
(b) dissolving or dispersing a slow release carrier and said purified tyrphostin in an organic solvent for obtaining an organic solution containing said carrier and said purified tyrphostin;
(c) adding said organic solution into an aqueous solution for obtaining an oil-in-water-type emulsion; and
(d) evaporating said organic solvent from said oil-in-water-type emulsion for obtaining a colloidal suspension of particles containing said slow release carrier and said purified tyrphostin.

30. The method of claim 29, wherein said slow release carrier is polylactic acid.

31. A stent comprising a substantially tubular body, the body is made of a material designed for slow release of a purified tyrphostin of a general formula:

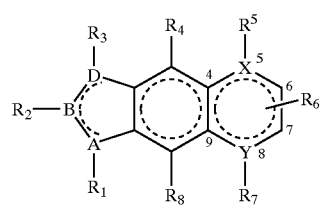

(Compound I)

wherein,
4, 5, 6, 7, 8 and 9 indicate positions on a terminal 6-member ring;
A, D, X and Y are each independently a nitrogen;
B is a carbon;
$R_1$, $R_2$, $R_3$, $R_5$ and $R_7$ are each independently selected from the group consisting of hydrogen, alkyl, alkenyl, alkynyl, cycloalkyl, aryl, hydroxy, alkoxy, halo, C-carboxy, O-carboxy, carbonyl, thiocarbonyl, C-amido, guanly, sulfonyl, trihalomethane-sulfonyl and a pair of electrons, or alternatively, $R_1$ and $R_2$ or $R_2$ and $R_3$ form a 5-7 member ring structure;
$R_6$ is selected from the group consisting of alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and a physiologically acceptable salt or a prodrug thereof;
$R_4$ and $R_8$ are each independently selected from the group consisting of hydrogen, alkyl, trihaloalkyl, cycloalkyl, alkenyl, alkynyl, aryl, heteroaryl, heteroalicyclic, hydroxy, alkoxy, aryloxy, thiohydroxy, thioalkoxy, thioaryloxy, sulfinyl, sulfonyl, N-sulfonamido, S-sulfonamido, trihalomethylsulfonamido, carbonyl, thiocarbonyl, C-carboxy, O-carboxy, C-amido, N-amido, cyano, nitro, halo, O-carbamyl, N-carbamyl, O-thiocarbamyl, N-thiocarbamyl, ureido, guanyl, guanidino, amino and —$NR_{10}R_{11}$ and, a physiologically acceptable salt or a prodrug thereof;

$R_{10}$ and $R_{11}$ are each independently selected from the group consisting of hydrogen, alkyl, cycloalkyl, aryl, carbonyl and sulfonyl, or alternatively $R_{10}$ and $R_{11}$ form a five- or six-member heteroalicyclic ring; and, a physiologically acceptable salt or a prodrug thereof;

whereas, for Compound I, said $R_6$ is either at position 6 or at position 7.

* * * * *